(12) United States Patent
Dawson et al.

(10) Patent No.: US 7,925,484 B2
(45) Date of Patent: Apr. 12, 2011

(54) METHOD FOR PREDICTING THE SPATIAL-ARRANGEMENT TOPOLOGY OF AN AMINO ACID SEQUENCE USING FREE ENERGY COMBINED WITH SECONDARY STRUCTURAL INFORMATION

(75) Inventors: Wayne Dawson, Yokohama (JP); Kazuo Suzuki, Isumi-gun (JP); Kenji Yamamoto, Tokyo (JP)

(73) Assignee: Wayne Dawson, Kanagawa (JP)

( * ) Notice: Subject to any disclaimer, the term of this patent is extended or adjusted under 35 U.S.C. 154(b) by 1851 days.

(21) Appl. No.: 10/695,247

(22) Filed: Oct. 27, 2003

(65) Prior Publication Data

US 2005/0090991 A1    Apr. 28, 2005

(51) Int. Cl.
*G06G 7/48* (2006.01)
(52) U.S. Cl. .............................. 703/11; 702/19; 702/27
(58) Field of Classification Search ........................ None
See application file for complete search history.

(56) References Cited

U.S. PATENT DOCUMENTS 5,424,963 A * 6/1995 Turner et al. .................... 703/6
6,832,162 B2 * 12/2004 Floudas et al. ................. 702/19

OTHER PUBLICATIONS

Tosatto et al., Current Pharmaceutical Design, vol. 12, 2067-2086, 2006.*
Dawson et al., J. Theor. Biol., vol. 213, p. 359-386, 2001.*
Alm et al. (Proc. Natl. Acad. Sci., vol. 96, p. 11305-11310, Sep. 1999).*
Bryngleson et al. (Proteins: Structure, Function, and Genetics 21:167-195 (1995)).*
2001, A Physical Origin for Functional Domain Structure in Nucleic Acids as Evidenced by Cross-linking Entropy: II, Wayne Dawson et al., J. theor. Biol., vol. 213, pp. 387-412.

* cited by examiner

*Primary Examiner* — Karlheinz R Skowronek
(74) *Attorney, Agent, or Firm* — Jordan and Hamburg LLP

(57) ABSTRACT

This invention is an algorithm for estimating the topology of a protein by determination of the free energy from a global entropy evaluation model combined with local correction methods.

9 Claims, 8 Drawing Sheets

(8 of 8 Drawing Sheet(s) Filed in Color)

METHOD FOR PREDICTING THE SPATIAL-ARRANGEMENT TOPOLOGY OF AN AMINO ACID SEQUENCE USING FREE ENERGY COMBINED WITH SECONDARY STRUCTURAL INFORMATION

BACKGROUND OF THE INVENTION

1. Field of the Invention

This invention is concerned with a novel algorithm for determining the spatial-arrangement topology of a protein from its secondary structure. The invention is an essential aid in finding the topology and ultimately the three dimensional (3D) structure of unknown protein structures. The invention also employs the algorithm to estimate the structural stability of a protein with a given secondary structure and sequence using a global entropy evaluation method combined with thermodynamic parameters obtained from experimental data of binding free energy (FE). The method also predicts the dominant folding pathway of a protein as a result of using this global entropy evaluation method.

2. Description of the Related Art

Determination of the three dimensional structure of a protein remains a very difficult process (1-5). The most successful approach is x-ray crystallography, which involves fitting diffraction data obtain at very large government-funded synchrotron facilities (1). Although academic professionals are able to apply for government funding to measure and analyze protein structures at such facilities, the costs of maintaining and operating such facilities that provide the beam time to support these experiments are prohibitively expensive and not accessible for commercial enterprises to fund. Moreover, biology related commercial enterprises need this information; particularly pharmaceutical companies where new drugs are always under development.

Furthermore, protein structures obtained by x-ray crystallography require skilled techniques to express and crystallize a given protein before such a measurement can be made (7, 8). It remains questionable whether all proteins can be crystallized and whether the crystalline structures fully represent the in vivo features of many biologically relevant proteins. Whereas many enzymes remain active even in this crystalline geometry (9), the true dynamics of these structures and the range of conformations can only be inferred in the x-ray data because the protein structures are rigidly locked in a crystal. The in vivo structures of protein subunits are even more difficult to assess as crystals.

A second approach is NMR spectroscopy (10, 11). NMR spectroscopy is cost efficient for a company to carry out. However, this technique is often fraught with difficulties due to the time resolution of NMR experiments, the effects of solvent exchange and other complex coupling effects (7, 8). In addition, the same problems that hamper x-ray crystallography research—protein expression, isolation, and characterization—also render this approach costly.

The easiest information to obtain accurately with NMR spectroscopy is the protein secondary structure (11). However, the protein secondary structure carries insufficient information to unambiguously identify the topology of a given protein (12).

The most important topological information gained by NMR experiments is the nuclear Overhauser effect (NOE) constraints (10-12, see also U.S. Pat. No. 6,512,997). One must first obtain many unambiguous NOE-constraints to obtain a successful prediction. However, many proteins have highly ambiguous NOE-constraints or the NOE signals are too weak and broad banded to properly assign. In such cases, the protein structure cannot be resolved by NMR and the only remaining option is to turn to x-ray crystallography.

A third approach is protein threading (13-20, see also U.S. Pat. Nos. 6,512,981; 5,878,373; 5,884,230 and 6,377,893). However, many proteins still have less than 25% homology with known protein structures in the protein data bank (PDB). To find a plausible template structure for a protein of 25% homology, considerably more information is needed to insure the accuracy of the prediction (13, 17) and there is no objective method for deducing which structures make acceptable threads.

A remaining option is to carry out a molecular dynamics (MD) simulation (21-26). Currently, molecular dynamics however, the time frame for a full protein refolding experiment remains intractable because of the long calculation times required from even the fastest computers (thousands of years even on a parallel processor supercomputer to achieve one ms of biological simulation time). Moreover, the uncertainties and ambiguities of even the state of the art MD simulation program render whatever conclusions can be made from such a long simulation questionable (21, 23-26).

Combinatorial folding models of secondary structure alone (27, 28) yield an intractable number of structural topologies to test in an MD simulation in explicit water (15, 26) If the correct topology can be obtained, the computational cost of an MD simulation is drastically reduced and the confidence level of the predictions improved to a root mean square (RMS) deviation of no more than 3 Å (29).

What is needed is an intermediate cost effective and objective approach that can infer the topology without having to wait several millennia for the answer to be produced, applying for large grants to budget synchrotron machine time, spending long hours in the lab searching for ways to isolate proteins, or utilizing subjective methodologies to infer the protein structure. The topology indicates how the secondary structure of a protein is arranged spatially and is the main juncture between the secondary structure and the full 3D structure. The topology (spatial arrangement) cannot be obtained from the three-state secondary-structure alone.

The invention is a semi-dynamic thermodynamic model of protein folding that we developed from RNA research (30) to account for the entropy of folding. Once the topology is known, a protein can be tested for its 3D structure with only a small fraction of the computer simulation time required for a complete protein refolding MD simulation. The invention is intended to aid the NMR and x-ray crystallographer in finding the 3D structure of an unknown protein based upon partially determined structural information, specifically the protein secondary structure.

The importance of gaining a foothold on protein topology cannot be emphasized enough. First, the experimental conditions that complicate the NMR experiments on proteins are generally the norm. Highly flexible proteins may have marginally stable secondary structures that make their structures difficult to determine experimentally with high precision by NMR. Second, functional proteins are dynamic entities, not static crystals (31, 32). For regions of structure that exhibit a high degree of flexibility and polar-regions where there is rapid solvent exchange, NMR spectroscopy is limited by its time resolution (10, 11). X-ray crystallography can obtain the structure of a protein that can be crystallized; however, the overall dynamics of the protein in solution are less clear. Topology prediction offers an independent tool to guide the structural determination and improve our understanding of the physics of protein structure and folding dynamics.

The folding model considers the direction in which biological proteins are synthesized and transported through the cell as a basis for considering the step-by-step thermodynamics of folding.

SUMMARY OF THE INVENTION

This invention is a method implemented as a program for estimating the topology of a protein based on the combined information of a global entropy evaluation model and local thermodynamic potentials that express hydrophobic, polar and electrostatic interactions as well as other corrections associated with size, shape or chemical properties. Parameters and models for these local thermodynamic potentials can be obtained from either theoretical sources, or from experimentally obtained data. The local interactions are modeled to help align individual protein secondary structure elements. Using a given amino-acid sequence and an obtained secondary structure estimate, the method is used to predict the best topology for the protein and to determine the dominant global folding kinetics of a protein in a biologically relevant fashion as described by the order and change in the protein's topology during optimization of the free energy where the synthesis of a protein is expected to be from the amino terminal (N-terminal) end toward the carboxy-terminal (C-terminal) end.

More concretely, the invention of this application is relating to a method to predict the topology of the spatial arrangement of an amino acid sequence using an entropy evaluation model that takes into account the global contributions of entropy to the folding of a biopolymer (herein referred to by the name cross linking entropy (CLE) and described in the literature) combined with other thermodynamic potentials as a protein-folding model.

Further, the invention of this application may comprise the following steps:

A. inputting an amino acid sequence of a protein,
B. preparing information on the secondary structure of the said amino acid sequence by way of at least one theoretical or experimental estimate,
C. applying the CLE method to the said amino acid sequence and secondary structure information to evaluate the free energy of a combinatorial number of β-strand and α-helix arrangements as rapidly as polynomial time: $c(n-1)(n+1)$ wherein c is a constant and n is the number of secondary structure elements found in the said amino acid in A and prepared in B,
D. applying the CLE method in conjunction with other thermodynamic potentials that approximate hydrophobic, electrostatic and polar interactions, but not limited to these aforementioned thermodynamic potentials stated herein, in a thermodynamic calculation to account for both short and long range folding interactions and predict a minimum free energy and corresponding topology of the said amino acid sequence,
E. applying the CLE method to predict the global folding kinetics of the said amino acid sequence, and
F. storing the information in a data file or in other form of digital memory.

In the invention of this application, the cross linking entropy (CLE), which is an entropy evaluation model that takes into account the global effects of entropy in the folding of a biopolymer, can be used to evaluate the entropy loss of a protein due to folding into a particular topology given a known secondary or estimated secondary structure.

Further, the invention of this application is relating to above-mentioned inventions, in which loss of biological activity of the protein can be further predicted.

Further, in the invention of this application, a initial theoretical estimate of the secondary structure can be obtained from either a theoretical source, an experimental source such as an NMR experiment or x-ray crystallography, or both.

The invention of this application further relates to above mentioned method, in which the theoretical estimate can be further supplemented with sequence alignment to find regions in which conserved segments remains essentially unchanged by differences in the aligned sequences.

In the invention of this application, the amino acid sequence and secondary structure-information can be used to evaluate the free energy of a combinatorial number of β-strand and α-helix arrangements as rapidly as polynomial time: $c(n-1)(n+1)$ wherein c is a constant and n is the number of secondary structure elements found in the said amino acid and obtained.

Further, the invention of this application is relating also to a method to predict the topology of the spatial arrangement of an amino acid sequence comprising following steps:

A. inputting an amino acid sequence of a protein,
B. preparing information on the secondary structure of the said amino acid sequence by way of at least one theoretical or experimental estimate,
E. applying the CLE method to approximate the global folding kinetics of the said amino acid sequence,
G. applying the CLE method to the said amino acid sequence and secondary structure information to reduce the combinatorial number of β-strand and α-helix arrangements to a computationally manageable number, and
H. applying the CLE method to optimize the free energy to find the most thermodynamically favorable topology for the said amino acid sequence, wherein the global free energy (FE) contribution from the CLE between two distinct amino acid residues, herein labeled i and j, is calculated by equation (1):

$$\Delta G_{ij} = -T\Delta S_{ij} = \frac{\gamma k_B T}{\xi} \left\{ \ln\left(\frac{2\gamma\xi\Delta N_{ij}}{3\lambda_{ij}^2}\right) - 1 + \frac{3\lambda_{ij}^2}{2\gamma\xi\Delta N_{ij}} \right\} \quad (1)$$

wherein, i and j represent the indices of two distinct residues in the said amino acid sequence, and j>i, $\Delta N_{ij}=j-i+1$ expresses the number of residues separating i and j, $\Delta G_{ij}$ is the difference in the free energy contribution to the CLE from residues i and j transitioning from the denatured (random flight) state to the native state, $\Delta S_{ij}$ is the corresponding entropy loss, ξ is the persistence length, γ is a dimensionless weight parameter describing the self-avoiding properties of a polymer chain, $k_B$ is the Boltzmann constant, T is the temperature, and $\lambda_{ij}$ (the bond gap) expresses the amino acid separation distance between the center of mass of residue i and the center of mass of residue j when both are treated as isolated molecules.

Here, the total CLE contribution to the free energy ($\Delta G_{cle}$) can be calculated by equation (2):

$$\Delta G_{cle} = \Delta G_\xi^o + \sum_{all\_bonds(i,j)} \Delta G_{ij} + \sum_{i',j'} f_{i'j'}(\xi) \quad (2)$$

wherein, $\Delta G_{ij}$ is defined in equation (1), i' and j' are indices specifying two secondary structure elements (α-helices or β-strands) that are joined together by the corresponding set of bonds i and j, $f_{ij}(\xi)$ is a positive definite penalty function used to enforce topology constraints on the minimum allowed sequence length of a loop connecting two elements of secondary structure i'j' and is a function of the persistence length ξ, and $\Delta G_\xi^o$ is a renormalization correction and is an integral function of ξ has shown by equation (3):

$$\Delta G_\xi^o = \frac{(\gamma + 1/2)Nk_BT}{D\xi} \int_{+1}^{\xi} \left( \frac{\ln(x)}{(1-x)} + 1 \right) dx \quad (3)$$

wherein, ξ, γ, $k_B$, and T mean the same as defined in the disclosure, N indicates the number of amino acids in the said sequence, D is the dimensionality of the system, the limits in the integral (1→ξ) indicate the change in the number of degrees of freedom from an individual amino acid reside to a cluster of ξ amino acids treated as a group (where ξ>1 amino acid and ξ need not be an integer) and x is dummy variable in the integral substituting for ξ.

In the invention of this application, the optimal β-sheet alignments can be obtained by using thermodynamics.

Further, the CLE method is applied in conjunction with other derived or constructed thermodynamic potentials that approximate hydrophobic, electrostatic and polar interactions, in a thermodynamic calculation to account for both short and long range folding interactions and predict a minimum free energy and corresponding topology of the said amino acid sequence.

The invention of this application is also relating to a method for building a 3D structure of a protein for MD simulation from the topology obtained by one of the above-mentioned method.

The invention is relating to a method to predict the topology of the spatial arrangement of an amino acid sequence using the entropy evaluation model, comprising the following steps:
A. obtaining an amino acid sequence of a protein,
B. preparing information on the secondary structure of the said amino acid sequence by way of at least one theoretical or experimental estimate,
E. applying the CLE method to approximate the global folding kinetics of the said amino acid sequence,
I. using the global folding kinetics to predict the optimal topology of the said amino acid sequence, and
F. storing the information in a data file or in other form of digital memory.

BRIEF DESCRIPTION OF THE DRAWING

The patent or application file contains at least one drawing executed in colour. Copies of this patent or patent application publication with colour drawings will be provided by the Office upon request and payment of the necessary fee.

The present invention may be more readily described with reference to the accompanying drawings, in which.

DESCRIPTION OF THE PREFERRED EMBODIMENT

Definitions and Background on Biopolymer Theory

Figure 1:
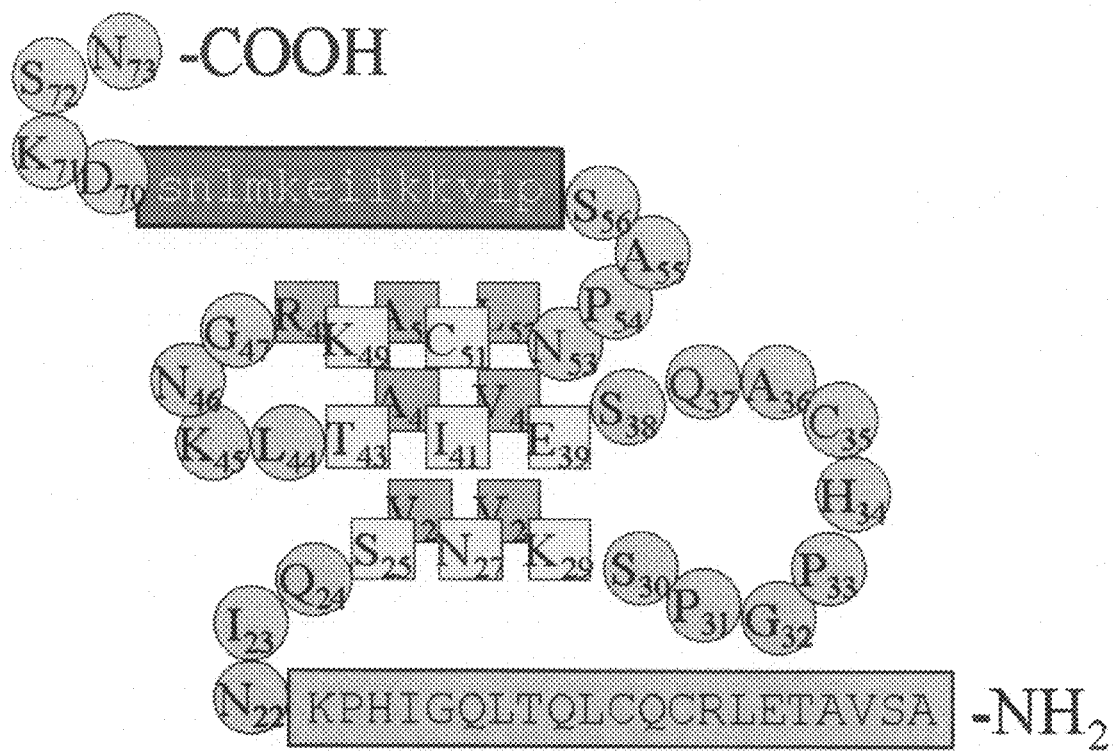
FIG. 1 shows IL-8 topology in the beta meander region. The yellow and orange squares represent residues in the β-strand regions whose rotors point out of the page and into the page respectively. The green residues are coil regions and red refers to α-helical regions.

We first present a brief summary of the concepts used within this work. Special words used in other parts of this work are given in double quotation marks " " when first encountered in this section. It is hoped that by seeing these words used in this context, the nearly interchangeable meaning of such expressions as 'entropy loss' and 'global entropy' will become clear. For further details and clarification on the theoretical concepts of biopolymer folding, reference 48 (although somewhat dated now) is very strongly recommended. Additional supplementary material can be found in such sources as A. Yu. Grosberg and A. R. Khokhlov, Statistical Physics of Macromolecules, AIP Press, Woodbury (N.Y.), 1994; and M. Doi and S. F. Edwards, The Theory of Polymer Dynamics, Clarendon Press, Oxford, 1986; and P. G. deGennes, Scaling Concepts in Polymer Physics, Cornell University Press, Ithaca, 1979. Another supplementary text important for understanding the concept of "renormalization theory" as used in this presentation can be gained from the first six chapters of J. J. Binney, N. J. Dowrick, A. J. Fisher, and M. E. J. Newman, The Theory of Critical Phenomena: an Introduction to the Renormalization Group, Clarendon Press, Oxford, 1992.

The word "cross link" is used in a very broad sense in this work to describe any type of bond (35). In proteins, typical bonding effects include hydrophobic interactions, covalent bonds such as the disulfide bonds, hydrogen bonds, and salt bridges. Each bonding effect is considered a cross-link in this model.

The entropy associated with the folding of a biopolymer is a statistical function associated with the number of conformations that are available to the biopolymer. For example, if we restrict ourselves to the three regions of the Ramachandran plot that correspond to the right-handed alpha helix region ($\alpha_R$), the β-sheet or extended region (β or ϵ), or the left-handed α-helix region ($\alpha_L$), then an N residue peptide has $3^N$ conformations available to it (excluding corrections for excluded volume). Even for such a grossly over-simplified model for the conformations, the number of possible conformation becomes astronomical for any reasonable sized protein.

Therefore, the problem is usually reduced to a much simpler model, the simplest and most transparent being the "random flight model" also known as the "Gaussian polymer chain" (GPC) model. In the GPC-model, the individual monomers (referred to here as "mers" for short) are reduced to mere formless particles akin to "beads on a string". Although very abstract and seemingly not highly representative of any real monomers, such models are able to approximate some important features of polymer dynamics.

The GPC-model expresses the statistical probability of finding a given end-to-end separation distance r for the first and last mer in the polymer sequence and is expressed as follows $$p_G(r) = C_n^1 r^2 \exp(-\beta r^2) \Delta r \quad (0a)$$

where $\beta = 3/(2\xi b^2)$, $C_N^1 = 4\pi(\beta/\pi)^{3/2}$, N is the number of monomers in the polymer chain, b is the separation distance between the monomers, and ξ is the persistence length expressed in units of monomer separation distance b. Clearly, $p_G(r)/4\pi r^2 \Delta r$ is the "probability density function (pdf)" of a Gaussian distribution. For ξ>1 mer, the persistence length indicates that the neighboring mer (or mers) within a distance ξ along the polymer chain exhibit "strong coupling" (meaning that the motion of these molecules is "highly correlated") and their motions will not be sufficiently independent to treat as distinct mers. For mers separated by a distance greater than ξ, there is only "weak coupling" between the respective mers (low degree of correlation) and the elements can be treated as approximately independent. The structure of the GPC takes the form of $\tilde{N}(=N/\xi)$ "beads" separated by a distance $\tilde{b}(=\xi b)$ where ξ mers are grouped into a single bead. It is easy to see that the root-mean-square separation distance between the first and last mer in Eqn (0a) is $r_o = b\sqrt{2\xi N/3}$ because Eqn (0a) is a Gaussian function.

The GPC model is too simple a model for a real polymer because it does not even consider that the polymer chain is "self-avoiding": a property in which no two mers of the polymer sequence can occupy the same spatial position at the same time (conservation of matter). The first approximation of a self-avoiding polymer chain consists of a variant of the "Gamma function" that has the form $$p_\Gamma(r) = C_\gamma r^{2r} \exp(-\alpha r^2) \Delta r \quad (0b)$$

where $\alpha = 3/(2\gamma \xi Nb^2)$, $C_N^r = 2(3/2N)^{\gamma+1/2}/\Gamma(\gamma+1/2)$, $\Gamma(\gamma+1/2)$ is the Gamma function, and γ is a dimensionless parameter for which γ=1 renders Eqn (0b) equal to Eqn (0a). For all known polymers, γ>1. Because of the nature of Eqn (0b), we call this a "Gamma polymer chain (Γ-PC)" and the respective function a "Gamma-pdf (Γ-pdf)".

For a system in which the size of the beads is the same as the mers, these pdfs permit us to express the entropy as follows $$\Delta S = S - S_o = k_B T \ln(p(r)) = k_B \{\ln(C_N^\gamma) + 2\gamma \ln(r/b) - \alpha r^2\} \quad (0c)$$

where $S_o$ is a reference entropy and constant, $\alpha = 3/(2\xi Nb^2)$ and we often refer to Eqn (0c) in this method as the "cross linking entropy (CLE)". The maximum in Eqn (0c) can be found by evaluating the force (f) as $f(r) = -T(\partial \Delta S/\partial r)$ and solving for the stationary point. Using this force equation, one finds a maximum at $r_o$, with the correct $r_o$ for Eqn (0a) (shown above) and $r_o = 2\gamma \xi b^2/3$ for the Γ-pdf. This shows that the maximum in the entropy of this model occurs at $r_o$ and for $r<r_o$ and $r>r_o$, the entropy decreases because fewer conformations are possible for the polymer chain. This decrease in entropy, due to restriction of conformations, is often called "entropy loss". This entropy (ΔS) is global because even when thousands or millions of mers separate the ends of the polymer chain, the correlation still increases where $r_o^2 \propto N$.

The formation of cross-links between the ends of the chain, r is compressed to some distance λb where λ is a dimensionless proportionality constant we refer to as the "bond gap".

The end-to-end correlation effects are not restricted to the terminal ends of the sequence. For a given monomer i and j (where i≠j and i<j), this weak coupling leads to a dependence in which $r_{ij}^2 \propto (j-i+1)b^2$. In the current embodiment, we use this to help estimate the entropy loss caused by the formation of bonds (or cross-links) between i and j. Furthermore, because we assume weak coupling between mers in the polymer chain separated by a distance ξ or greater, the coupling between a cross-link (bond) formed between mers $i_1$-$j_1$ and that of $i_2$-$j_2$ is sufficiently weak that they can be treated as independent permitting us to approximate the "global entropic contribution" by a summation. The summation of all the global entropic contributions is what we call the "total (global) entropic contribution". For mers separated by a distance less than ξ, we apply "renormalization group theory" in which these mers are grouped as though they behaved as a single monomer of fractional size 1/ξ. Approximations and corrections that account for this grouping are developed from this theory. Again, if the beads and mers exactly correspond in number, the global entropic contribution formers i and j is similar to Eqn (0c)

$$\Delta S_{ij} = S_{ij} - S_{ijo} = k_B T \ln(p(r_{ij})) = k_B \{\ln(C_{ij}^\gamma) + 2\gamma \ln(r_{ij}/b) - \alpha r_{ij}^2\} \quad (0d)$$

where $C_{ij}^\gamma$ and $C_N^\gamma$ have essentially the same meaning except that in Eqn (0d) likewise $S_{ijo}$ and $S_o$, N=j-i+1 (where j>i is assumed). When the more likely situation is found where mers i and j do not correspond exactly to the bead size (ξ>1), Eqn (0d) is weighted by a factor 1/ξ to account of this "renormalized contribution" of mers i and j to the global entropy. Weighting Eqn (0d) by 1/ξ amounts to taking the "average contribution" of the group of mers to the global entropy of the beads.

The "free energy (FE) contribution" from this "global CLE contribution" for the interaction of mers i and j is therefore $\Delta G_{ij} = -T\Delta S_{ij}$, and this FE, when viewed from the perspective of folding a biopolymer from its entropy maximum ($r_o$) to some small distance ($r=\lambda b$), can be seen to yield a positive value. Since the free energy must be negative to be considered spontaneous, a positive entropic contribution to the FE can be understood to be a "free energy cost", since some other interaction must make up the difference in the free energy to insure that the reaction remains spontaneous.

In general, a "global entropy evaluation" of the effects of correlation between mer i and mer j is a function of the allowed conformations of the polymer change due to its chemical and mechanical properties. It is not a fully settled issue as to what extent complex systems such as a heterogeneous biopolymer can be simplified to a mere summation of the respective global entropic contributions corrected over a persistence length $\xi$. More forms of correlation might be anticipated than are currently addressed with the Γ-pdf. Therefore, in its most general form, the global entropic contribution or CLE between residue i and j of a protein is currently an unknown function. In the current embodiment, this function has been approximated by the Γ-pdf subject to corrections for $\xi > 1$ mer. Other local interactions such as hydrophobic, charged and polar conditions are also assumed to be sufficiently weakly coupled so that they can be resolved at the monomer or at most the dimer level.

In summary, the general form of the CLE should not be assumed to be a Γ-pdf. However, for practical reasons of computation, the Γ-pdf is used to evaluate the CLE in the embodiment and examples given here. As long as one can find some way to write some description of the CLE in terms of either the beads or the mers, the method for evaluating the CLE, the assumptions, the approximations, and the procedures used in evaluating the free energy of the biopolymer ("the CLE method") will amount to the same procedure.

Theoretical Secondary Structure Predictions

Prior to use of this invention to determine the topology of the protein, information on the secondary structure is required.

Determination of the secondary structure can come from a variety of sources. Theoretical estimates can be obtained from such sources as PredictProtein (33-37), Jpred (38, 39), the secondary structure predictions from 3Dpssm (40, 41), NNpredict (42, 43), or PSIpredict (18-20). These theoretical estimates can be further supplemented with sequence alignment obtained from BLAST (and PSI-BLAST) to find regions in which conserved segments such as the hydrophobic core (in particular) remains essentially unchanged by differences in the aligned sequences. Secondary structure information can also come from an NMR experiment or x-ray crystallography.

The Protein Folding Model: Cross-Linking Entropy (CLE)

For questions on algorithms discussed in this section, the reader is referred to the following reference book. G. F. Luger, Artificial Intelligence: Structures and Strategies for Complex Problem Solving, 4$^{th}$ ed. Person Education Ltd, Essex, 2002 and P. A. Pevzner, Computational Molecular Biology: an Algorithmic Approach, MIT Press, Cambridge (Mass.), 2000.

Levinthal's Paradox points out that if a protein must search all the possible conformations available to it, even a simple protein would take much longer than the lifetime of the universe to fold (44). To eliminate this large conformation space, nature must reduce the number of degrees of freedom in the folding process and the free energy should be such that folding has a funnel shape (44-47). In the model, these degrees of freedom are expressed in the persistence length ($\xi$) (48). A very stiff structure would have a long persistence length, would tend to remain correlated over several amino acids and would fold as a unit rather than as individual residues (30, 47, 48). In the model, it is assumed that there are no significant kinetic traps (5, 9) and that the denatured state of a protein (4, 49) can be approximated by a random flight approximation (30). We have shown that the CLE successfully models the global folding of RNA in conjunction with the thermodynamic parameters that are currently in use for these structure calculations (30). Whereas the detailed packing rules of protein folding are fundamentally different from RNA (50), the entropy associated with the global folding conformations of a biopolymer can be treated as independent of the details of the particular system in the first approximation (48).

The CLE method helps to simplify the problem of calculating the topology of the protein. There are several ways in which this is accomplished.

First, the amino acids are grouped in units of length $\xi$, where $\xi$ could be treated as a variable if more information is known about the flexibility of the biopolymer. Units of length $\xi$ are of the same order as the length as the secondary structural units. Hence, the problem of handling N weakly coupled mers is reduced to one of handling approximately $2 \times N_{ss}$ weakly coupled beads. This drastically reduces the problem of solving a $3^N$ conformation problem to a much simpler one of beads on a string.

Second, in applying the CLE, it is assumed that the three state secondary structure (i.e., α-helix, β-strand, coil) is precisely known and we have only to consider how it is to be arranged in the folding process. At least 70% of the secondary structure can be predicted based on primary sequence data alone, and can be increased up to 80% by using sequence alignment techniques (33).

However, if no topological restrictions are applied in the folding problem, the number of ways in which $N_{ss}$ secondary structure elements can combine is factorial ($2^{N_{ss}-1}N_{ss}!/2$). Hence for 8 secondary structure elements, there are more than 2.5 million ways these structures could combine. To reduce the number of untenable combinations of β-strands to a manageable number, we use the CLE method to help deduce the global folding of the β-strand regions.

Therefore, a third aspect of this method is the way in which folding is carried out. In the RNA problem, we have found that a branch and bound algorithm is sufficient for describing the folding of RNA. The reason is that RNA folds from the 5' to the 3' end and therefore, it is actually folding during synthesis or as it is transported through a biological membrane. A similar situation occurs in a protein where the synthesis and transport proceed from the N-terminus to the C-terminus. Therefore, in the limiting case, the branch and bound approach is sufficient to solve this protein-folding problem within the CLE model. However, the branch and bound method still exhibits exponential growth in computer resource. The theory developed from the CLE shows that for such structures as pleated β-sheets are strongly favored entropically compared to other conceivable structures such as a jellyroll fold. Protein folds such as the Greek-key or the jellyroll fold are rare compared to β-meanders. The reason is due to entropy. (A similar situation can be posited in the folding of adjacent α-helices in such proteins as cytochrome C.) A picture emerges in which the folding of a protein is quite rapid, and the dynamics are such that a protein effectively "grabs" the closest neighboring secondary that exhibits a reasonably favorable FE. Since the closest neighbor is likely to be the next adjacent strand, it should be no wonder why the β-meander structure is so common in protein folds (refs 1-3, and although quite dated, we also recommend G. E. Schulz and R. H. Schirmer, Principles of Protein Structure, Springer-Verlag, New York, 1979). Evolution has further fine-tuned this folding so as to usually produce a thermodynamically stable structure that can also be obtained through refolding (where N-terminus to C-terminus folding should not be assumed but rather nucleation). The length of many proteins is often in the range of 200 amino acids or less. Secondary structure elements are typically on the order of 5 amino acids in length (similar to $\xi$), and most often, only half of the protein sequence forms secondary structure. This means that for a 200 amino acid protein, there are about 20 secondary structure segments. The jellyroll fold, one of the most complex in protein folding groups is composed of only six $\beta$-strands. This means that the scan region for folding can be limited to about 8 elements in the first step. A recursive search (without replacement) can then be employed that preserves the dominant order in which the secondary structure units combine. Unlike the time it takes for the protein to fold, which is an exponential function of the global entropy (see example 5, Eqns (4) through (7)), the recursive search (without replacement) is done in polynomial time. If the secondary structures are all of the same size, then the time to align individual mers can be treated as a constant $(A_t)$ times the recursive search (without replacement) of the secondary structure elements or $t_{search} \propto A_t B(N_{ss}+1)(N_{ss}-1) \propto N_{ss}^2$ where B is a constant and $\max\{A_t\} \propto \xi^3$ (depending on the procedure and assumptions used to evaluate $A_t$). This is a substantial gain over other methods. The underlying assumption in the CLE model is clearly that proteins don't wait a long time to find their fold. In the event that much longer folding times are thought to occur, a branch-and-bound approach is also an option.

We now discuss how the cross linking entropic contribution to the free energy (FE) is evaluated as it pertains to using the Gamma polymer chain equation with no loss of generality for other methods that can express the entropy relationship between two residues i and j in an additive fashion. The total FE refers to the summation of the individual contributions of bonds (cross-links) i and j. In the current embodiment, $\xi$ is treated as though it were a constant. However, the expressions can be modified to consider a variable $\xi$, if an experimental or theoretical estimate is available.

The global entropic free energy cost for folding a denatured protein into a $\beta$-sheet structure is expressed as follows. Let i and j represent the indices of two distinct residues in a protein sequence, where j>i. The number of residues separating i and j is $\Delta N_{ij} = j-i+1$. The global FE contribution from the CLE of residues i and j can be approximated by the following expression $$\Delta G_{ij} = -T\Delta S_{ij} = \frac{\gamma k_B T}{\xi}\left\{\ln\left(\frac{2\gamma\xi\Delta N_{ij}}{3\lambda_{ij}^2}\right) - 1 + \frac{3\lambda_{ij}^2}{2\gamma\xi\Delta N_{ij}}\right\} \quad (1)$$

where $\Delta G_{ij}$ is the difference in the free energy contribution to the CLE from residues i and j transitioning from the denatured (random flight) state to the native state, $\Delta S_{ij}$ is the corresponding entropy loss, $\xi$ is the persistence length, $\gamma$ is a weight parameter describing the self-avoiding properties of a polymer chain ($\gamma$=1.75 in three dimensions; Ref. 51), $k_B$ is the Boltzmann constant, T is the temperature, and $\lambda_{ij}$ (the bond gap) expresses the amino acid separation distance between residues i and j in the native state. Typical values for $\xi$ are on the order of 3 amino acids, but $\xi$ is highly sequence and structure dependent and can be much longer.

The total CLE contribution becomes the sum of each $\Delta G_{ij}$ contribution to the native state, $$\Delta G_{cle} = \Delta G_\xi^o + \sum_{all\_bonds(i,j)} \Delta G_{ij} + \sum_{i',j'} f_{i'j'}(\xi) \quad (2)$$

where $\Delta G_{ij}$ is defined in Eqn (1), i' and j' are indices specifying two secondary structure elements ($\alpha$-helices or $\beta$-strands) that are joined together by the corresponding set of bonds i and j, $f_{i'j'}(\xi)$ is a positive definite penalty function used to enforce topology constraints on the minimum allowed sequence length of a loop connecting two elements of secondary structure i'j' and is a function of the persistence length $\xi$, and $\Delta G_\xi^o$ is a renormalization group correction and is an integral function of $\xi$, $$\Delta G_\xi^o = \frac{(\gamma + 1/2)Nk_B T}{D\xi}\int_{+1}^{\xi}\left(\frac{\ln(x)}{(1-x)} + 1\right)dx \quad (3)$$

where N indicates the number of amino acids in the said sequence, D is the dimensionality of the system, the limits in the integral (1→$\xi$) indicate the change in the number of degrees of freedom from an individual amino acid reside to a cluster of $\xi$ amino acids treated as a group (where $\xi$>1 amino acid and $\xi$ need not be an integer). The value of $\Delta G_\xi^o$ can also be found by fitting with the aid of experimental reference data. The contribution $\Delta G_\xi^o$ accounts for the fact that we have grouped individual residues together and therefore reduced the number of degrees of freedom available to the peptide sequence (30).

The global CLE is a function of the likelihood that a polymer would spontaneously adopt a specified configuration represented by Eqn (2). Each cross-link adds to the global configuration entropy according to Eqn (2). This results in a cumulative (integral) effect that grows as $\Delta N_{ij} \ln(\Delta N_{ij})$. Ultimately this limits a domain or loop size because the CLE grows logarithmically $\{\ln(\Delta N_{ij})\}$ with each cross-link whereas the individual hydrophobic interactions are local and independent of $\Delta N_{ij}$. The CLE has shown considerable progress in addressing the folding of RNA (30).

In our current global CLE evaluation strategy, we assume the hydrophobic effect is the dominant feature that leads to attraction between different secondary structure elements of the protein sequence (50, 52). Thermodynamic parameters are dealt with based upon thermodynamic potentials in the local regime (52, 56-59). Structure is considered from standard models (3, 60-66). To help to orient the secondary structure, we use the polar, non-polar and hydrophobic interactions between neighboring $\beta$-sheets to help align the secondary (3, 56). Hydrophobic parameters can be obtained from such sources as Ref 45). Other parameterizations can be either resolved based on approximations from molecular dynamic simulations, or various theoretical or experimental sources.

To help to orient the $\beta$-strands, we use the polar, non-polar and hydrophobic interactions between neighboring $\beta$-sheets to help align the $\beta$-strands since these are likely to help stabilize the structure (3, 56). Scales of hydrophobicity can be obtained from such experimental sources as Y. Nozaki and C. Tanford, J. Biol. Chem. 246; 2211-2217 (1971) and references therein to name one. Theoretical sources could be for example T. Lazaridis, J. Phys. Chem. B, 102:3531-41 (1998). Other parameterizations can be either resolved based on approximations from molecular dynamic simulations, or constructed from some first principle approach.

This later approach follows a similar strategy first used by Cohen et al. (27, 28) to find ways to arrange β-sheets together: termed β-sheet alignment. As Cohen et al. reasoned, the alignment of residues should follow sensible relationships for neighboring residues along a pleated β-sheet region such as similar hydrophobicity, complimentary acid/base interactions, etc. (56-59). The improvement here is that we use this entropy to eliminate the multitude of combinations to a single topology or a finite set of solutions if dominant suboptimal structures are considered. Moreover, in this invention, the optimal β-sheet alignments are obtained by using derived (or estimated) thermodynamic potentials rather than statistical relationships between different proteins. A statistical relationship approach would be a possible alternative in a tuned potential; however, mere statistical relationships provide limited insight on the origin of the effects or what contextual aspects influence the uncertainty whereas physical models provide a conceptual framework that can be improved upon with better understanding.

A similar strategy is applicable in the case of α-helices. The major difference is that the residue alignments between two secondary structures much coincide with the cylinder shape of an α-helix. Thus the contact points of residues along this face have gaps {i, i+1, i+4, i+5, i+8, i+9} where i is a reference position of the beginning of an α-helix (27, 28).

The protein folder works on the principle of crawling along the sequence from the N- to C-terminus searching for the nearest acceptable β-strand that permits the minimum entropy loss, balanced with favorable hydrophobic and ionic interactions. In this respect, the protein folder assumes that a protein folds as it is extruded from such biological structures as the ribosome rather than assuming that the protein specifically folds from the denatured state.

The algorithm currently is primarily concerned with fitting all β-sheet proteins of approximately 70 amino acids in length. Longer sequences can in principle be solved using this approach with varying degrees of success in its current form.

EXAMPLES

Explanation of practical example is shown as follow.

Example 1

When the invention is applied to a standard β-meander protein such as IL-8 (melanoma growth stimulating activity: 1 MGS), the correct topology is obtained. Table 1 shows the best residue alignment and topology found in the calculation (67).

TABLE 1

A calculation result of the topology of IL-8 (a known structure) using the invention. The '_' indicates that no residue neighbors the region in a β-strand orientation.

D1mgsa, IL-8
number of beta strands: 3

| strand | N | C | r_j | f_i | f_j | p |
|--------|----|----|-----|-----|-----|-----|
| 1 | 25 | 29 |  | 1 | 2 | b- |
| 2 | 39 | 43 | 1 | 2 | 3 | b- |
| 3 | 48 | 52 | 2 | 3 |  | b- | strand 1 + 2: 25-43, 26-42, 27-41, 28-40, 29-39
strand 2 + 3: 39-_, 40-52, 41-51, 42-50, 43-49, _-48

In the top section of Table 1, the left most column indicates the index of the given β-strand segment of the amino acid sequence. The next two columns indicate the position at the N-terminus (N) and the C-terminus (C) of the β-strand. The next three columns indicate the determined topology of the protein sequence. The middle column labeled f_i (forward strand i) contains all the β-sheet indices. The column immediately to the left (r_j: reverse strand j) indicates the β-strand immediately adjacent to f_i whose index is less than i. Likewise, the column immediately to the right of f_i (f_j: forward strand j) indicates the β-strand immediately adjacent to strand i whose index is greater than i. The final column indicates whether the two β-strands that form the loop from antiparallel or parallel β-sheets (b—means antiparallel beta).

For a β-meander, the middle row (1 2 3) indicates that strand #2 has strand #1 to one side and strand #3 on the other. (In the topology, the axis of symmetry is two fold degenerate)

The bottom part of the table indicates the detailed topological arrangement of the mers in the β-strands relative to each other. The amino acids associated with strand i are denoted by $i_k$ where k specifies an individual amino acid in secondary structure i and similarly for $j_k$. The expression $i_k$–$j_l$ indicates that the residues ($i_k$ and $j_l$) from each strand (i and j) are directly adjacent to each other.

The topology and physical alignment of the β-strand residues is shown graphically in the FIG. 1 as a cartoon. The yellow and orange squares indicate rotors pointing out of the page and into the page. The predicted alignment and topology corresponds exactly with that of the known structure 1 MGS. It can now be inferred that since our protein folder works from the N-terminus to the C-terminus, the thermodynamic folding of this structure also occurs in the order strand #1-strand #2, follow by binding strand #2-strand #3. In a refolding experiment, both structures should form nearly simultaneously. If a branch-and-bound algorithm is used, then a refolding experiment can be mimicked. It has been found that RNA folds much faster when it is allowed to fold in the biologically relevant way, suggesting that these rules are applicable even to RNA biopolymers (S. L. HEILMAN-MILLER and S. A. WOODSON, Effect of transcription on folding of the Tetrahymena ribozyme RNA 2003 9: 722-733).

Example 2

Figure 2:
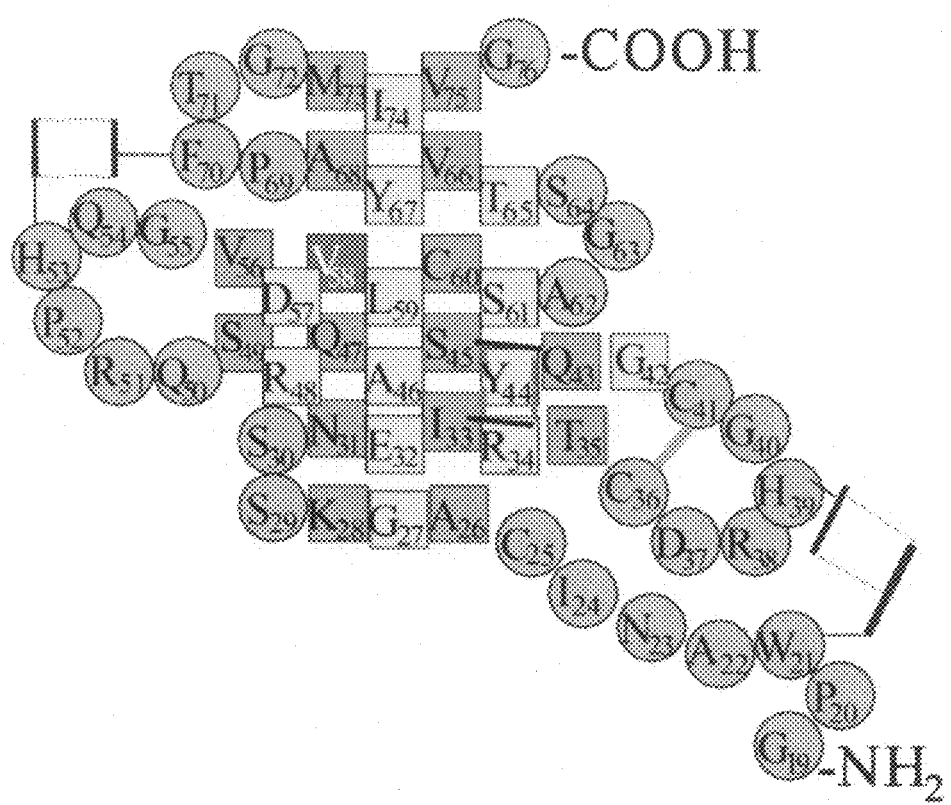
FIG. 2 shows LECT2 topology in the β-sheet region. The yellow and orange squares represent residues in the β-strand regions whose rotors point out of the page and into the page respectively. The green residues are coil.

Similar to example 1, the structure of an undetermined protein LECT2 is also calculated using this model (68, 69). Again, the topology is indicated in Table 2 in a similar way and a cartoon of the alignment and topology is shown in FIG. 2 (as an example).

TABLE 2

A calculation result of the topology of LECT2 (an unknown structure) using the invention. The '_' indicates that no residue neighbors the region in a β-strand orientation.

LECT2
number of beta strands: 6

| strand | N | C | r_j | f_i | f_j | p |
|--------|----|----|-----|-----|-----|-----|
| 1 | 26 | 28 |  | 1 | 2 | b- |
| 2 | 31 | 35 | 1 | 2 | 3 | b- |
| 3 | 42 | 49 | 2 | 3 | 4 | b- |
| 4 | 56 | 61 | 3 | 4 | 5 | b- |
| 5 | 65 | 68 | 4 | 5 | 6 | b- |
| 6 | 73 | 75 | 5 | 6 |  | b- | strand 1 + 2: 26-33, 27-32, 28-31
strand 2 + 3: _-42, 35-43, 34-44, 33-45, 32-46, 31-47, _-48, _-49

TABLE 2-continued

A calculation result of the topology of LECT2 (an unknown structure) using the invention. The '_' indicates that no residue neighbors the region in a β-strand orientation.

LECT2
number of beta strands: 6

| strand | N | C | r_j | f_i | f_j | p |
|---|---|---|---|---|---|---| strand 3 + 4: 49-56, 48-57, 47-58, 46-59, 45-60, 44-61, 43-_, 42-_
strand 4 + 5: 56-_, 57-_, 58-68, 49-67, 60-66, 61-65
strand 5 + 6: 68-73, 67-74, 66-75, 65-_

For LECT2, there are 6 β-strands and the alignment also has the form of a pleated β-strand structure. The pleated β-sheet fold and the β-meander fold are some of the most common structural motifs in the protein β-strand architecture (1-3). Examples 3 and 4 show how this topology can be used to find the 3D structure of the LECT2 protein. The topology of LECT2 is shown graphically in FIG. 2.

Example 3

Combining NMR Chemical Shift Data with Topology Information

Figure 3:
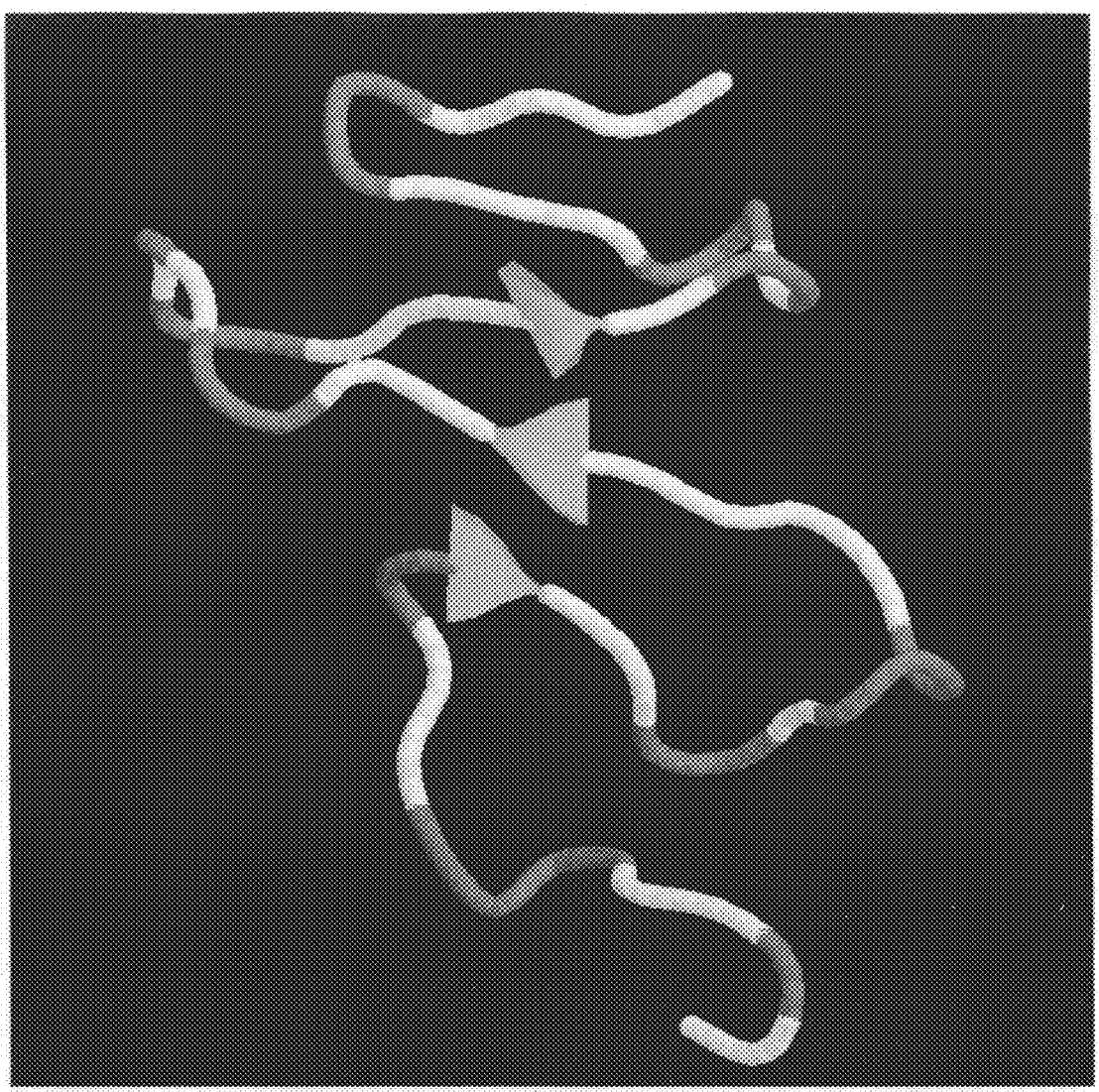
FIG. 3 shows the resulting structure of obtained by MD simulation and constraints of NMR secondary structure in conjunction with the calculated topology data of LECT2, based on NMR constraints.

NMR chemical shift data can now be used to evaluate the topological prediction by utilizing torsion angles estimates using such software as Talos (72, 73) and weighting the predictions relative to the certainty of the Ramachandran angles using a power law such as $x^n 10^{n-2}$, where x is the ratio of matching predictions to the best 10 predictions in the Talos database and n>6. An example of a prediction using this combined method is shown in FIG. 3.

Example 4

Building a Trial 3D Structures for MD Simulation

Once a topology is obtained from this invention, the 3D structure can be built and refined through dynamical simulations using a number of approaches, for example Refs 29 and 47.

To fold the amino acid sequence into the correct secondary structure and topology, the structure is first built in extended form to mimic the approximate configuration of the $P_{II}$ structures found in denatured proteins (31, 70, 71).

To introduce the secondary structure, torsion constraints are applied over the regions of secondary structure forcing out the secondary structure in the sequence using relatively strong torsion constraints on the order of $k_\theta=10$ kcal/mol·rad$^2$ with a maximum potential energy (PE) of 100 kcal/mol, where $k_\theta$ is the torsional force constant. To make the proposed contacts, weak distance constraints are then applied: $k_r \leq 2.0$ kcal/mol·Å$^2$ (max. PE≤10 kcal/mole), where $k_r$ is an effective spring constant. These distance constraints are typically applied to the C=O . . . H bonds. The structure is then allowed to relax during an MD simulation (either in explicit water or in vacuo) using simulated annealing starting from a high temperature (at least 400 K for at least 10 ps). The simulation time is doubled with each decrease in the temperature in a fashion akin to Newton's law of cooling. High temperature runs (T>600 K) required $k_r$>1 kcal/mol·Å$^2$, but annealing at lower temperatures can be done with $k_r$<1 kcal/mol·Å$^2$. To help minimize the effect of large fluctuations in the structure at high temperatures, the time increment should be set to 0.125 fs and strong torsion constraints should be placed on all the amide bonds to restrict the orientation in a trans configuration. For temperatures below 410 K, the time increment can be set to 0.5 fs. This annealing process should be applied over a period of 0.5 to 1 ns. The approach differs from Refs. 29 and 45 in that we recommend using small distance constraints ($k_r$<2. kcal/mol·Å$^2$ versus 100 kcal/mol·Å$^2$) and applying them over long and graduated simulated annealing times (preferably in excess of 200 ps) so that the structures have considerable time to explore the local conformation space. We also recommend starting with the $P_{II}$ conformation or an extended structure.

The very high temperature permits sufficient thermal energy to help fix some of the mis-oriented residues in the turns. At 300 K, the distance constraints are reduced to 0.5 kcal/mol·Å$^2$ (max 1.0 kcal/mol) and the simulation is run for 100 ps to help the structure further relax. After annealing in the water bath, all topological constraints can be removed and the structure is allowed to relax at 300 for 100 ps.

Figure 4:
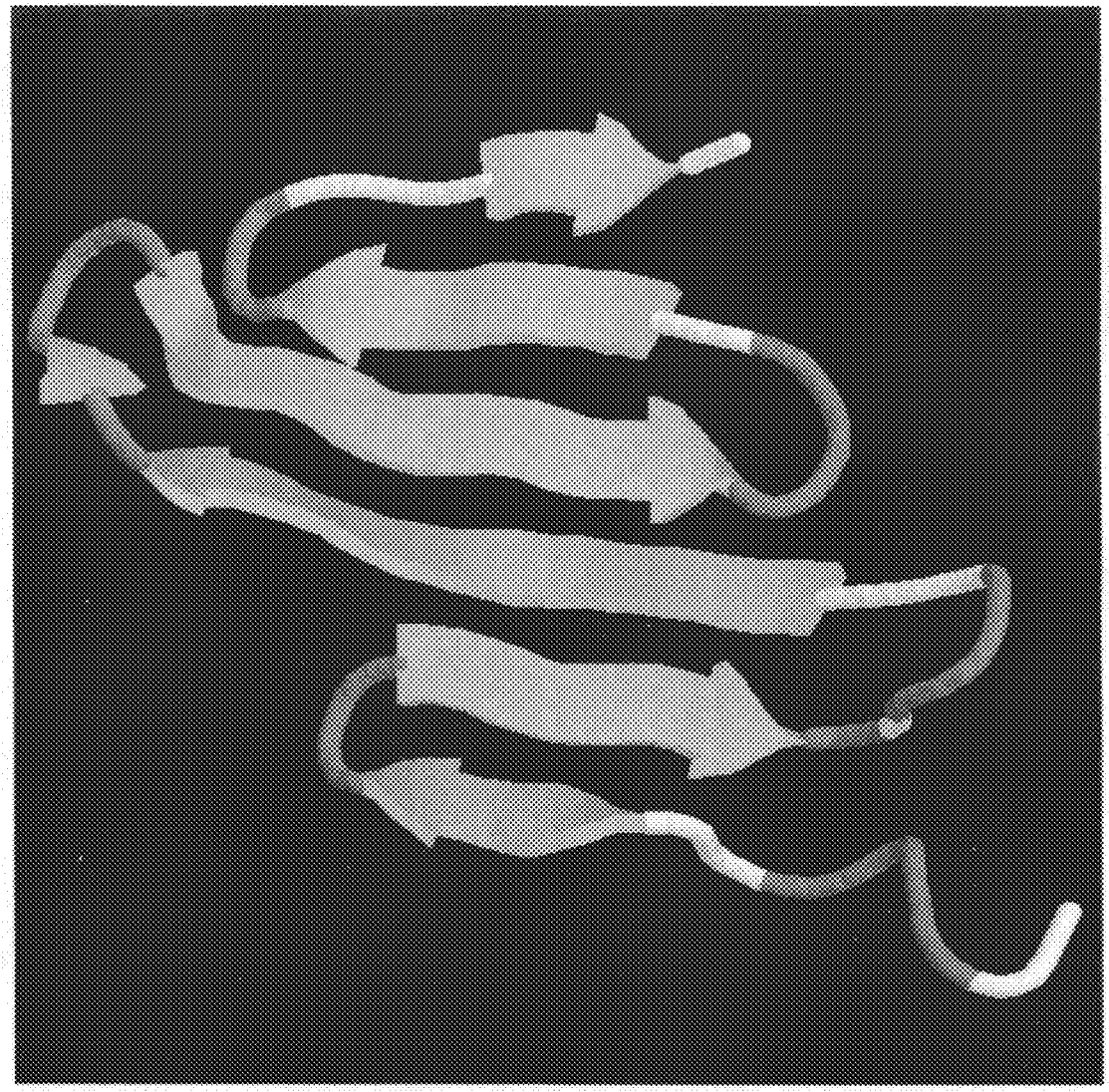
FIG. 4 shows the 3D structure of LECT2 after refining the NMR data further using information about the topology (after 300 ps simulation). The structure in FIG. 3 is also the same shape, but there is considerable variation in the positions of the amino acids.

FIG. 4 shows an example of the 3D structure of the LECT2 protein built in this way.

Example 5

Folding Principles of Various Structures

Figure 5:
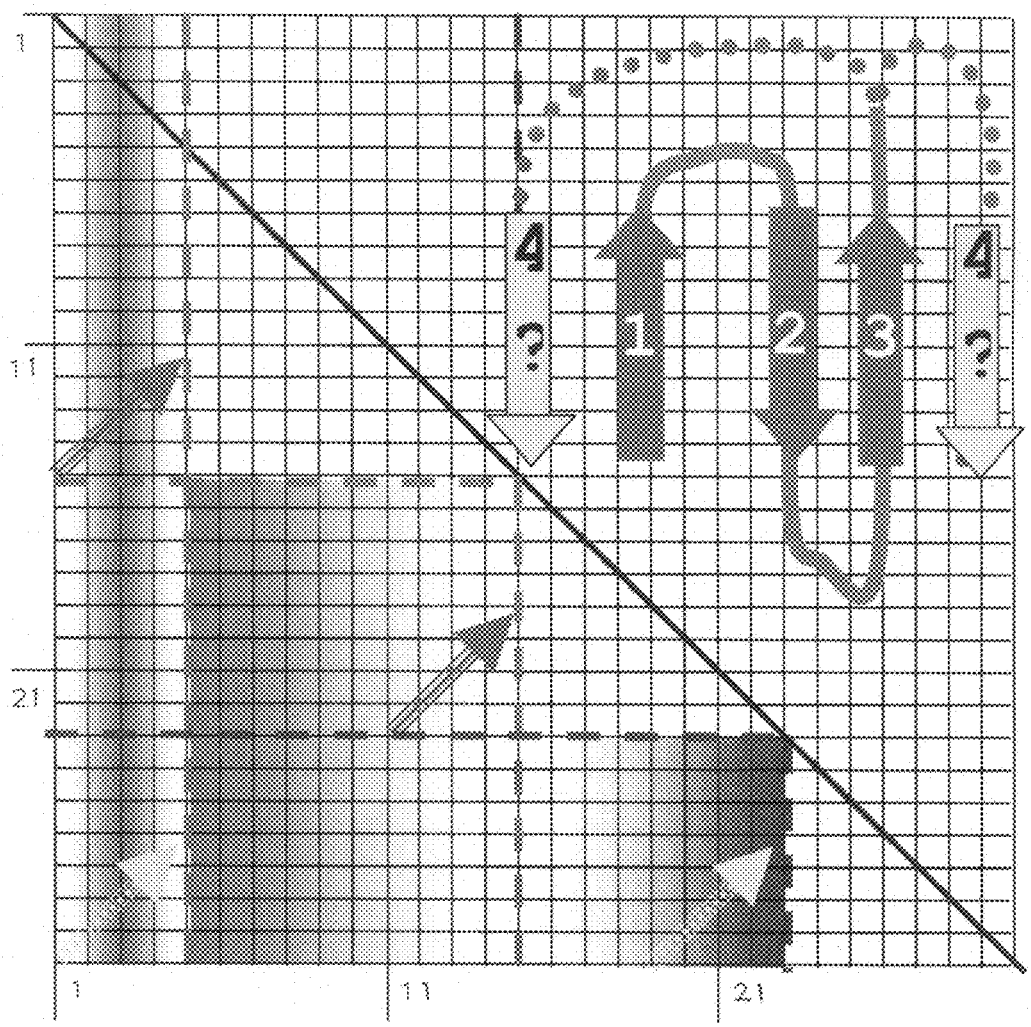
FIG. 5 shows topology and mapping of an antiparallel beta sheet structure. In the top right hand corner is a cartoon of the topology of an anti-parallel β-sheet protein. The β-sheets are assumed to be located at the amino acid positions (1-5), (11-15), (19-23), and (26-30), where, for example, the dash in (1-5) indicates residues between residue 1 and residue 5. The red region indicates the areas of the map that involve the formation of the β-meander (strands 1, 2, joining 3). The blue region marks off the areas of the map where a β-strand can form to the right hand side of the cartoon, and the green region indicates areas where the β-strand can form on the left hand side of the topology cartoon. The global entropy strongly influences this joining, and for such a short turn region (residues 24 and 25), it can be inferred that the entropy will select the right hand side. For a long coil region, the entropy is likely to predict the left hand side, unless there are strongly incompatible residues in these locations.

To help illustrate the folding model, in FIG. 5, a β-meander cartoon structure forms the central region labeled 1, 2 and 3 on the top right hand corner of the figure. In this example, the amino acid secondary structure is assumed to consist of the following strands: $\{1\sim5\}_1$, $\{11\sim15\}_2$, $\{19\sim23\}_3$, and $\{26\sim30\}_4$, where the notation $\{i_1\sim i_n\}_i$ indicates the specific indices of the amino acid fragment comprising the segment of secondary structure. The tilde indicates the set of amino acids that occupy that fragment of the sequence. On the left-hand side is the representation of the structure on a two dimensional (2D) graph (3). Each row corresponds to an index i and each column to an index j.

The β-strands 1, 2, and 3 are already decided in the structure. However, one must chose how to arrange the fourth strand. If the coil residues between the strands is very long, then $\lambda_{ij}$ will be large in Eqn (1) and the structure can fold to the left (depending on the composition of the β-strand at 1). On the other hand, if the sequence length is short, then the structure is likely to fold to the right. The possibilities are depicted in the triangle graph by the yellow arrows. The topological constraint function ($f_{ij}(\xi)$) will force β-strand 4 to link with strand 3 if the adjoining sequence is too short to permit crossing over to strand 1. In this case, stretching of the Gamma pdf ($r > r_o$) will result in a large positive entropy as well.

Protein folding can be largely limited to short range binding covering at most 10 secondary structure elements before settling into a structure. This is unique part of our invention. The CLE sets a limit on domain size due to the heavy weight of entropy loss. Topological restrictions such as the length of the loop region further restrict the allowed structures eliminating pointless combinatorial alignments when a connecting strand is shorter than a specified length.

Figure 6:
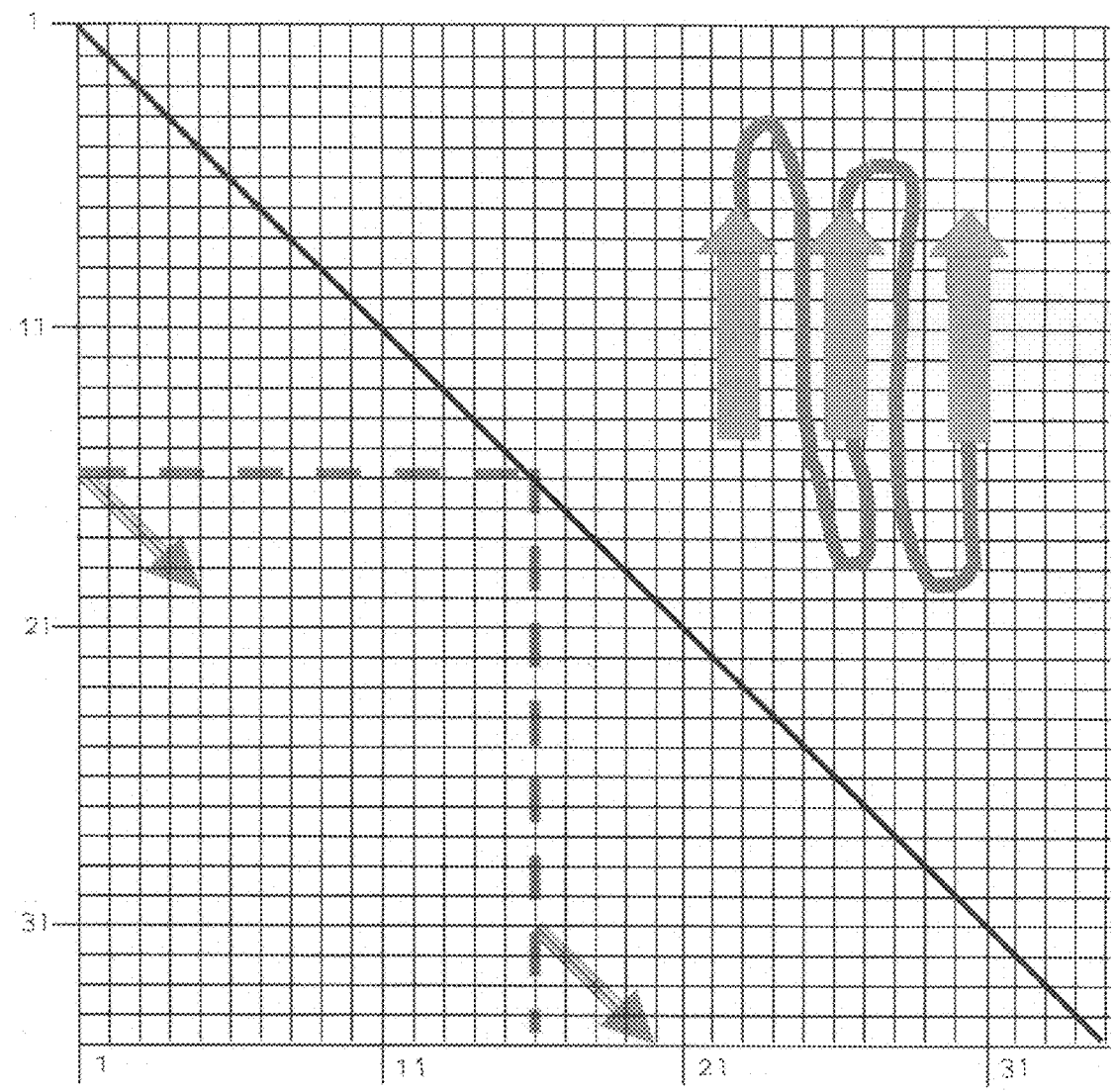
FIG. 6 shows an example of a parallel beta sheet structure. The cartoon at the top right hand corner is used in the same way as FIG. 1. The sequence consists of beta strands located at (1-5), (16-20) and (31-35). It can be seen that the direction of the beta strand linkages are different from FIG. 1. These are the primary distinguishing features between parallel and anti-parallel beta-sheets.
Figure 7:
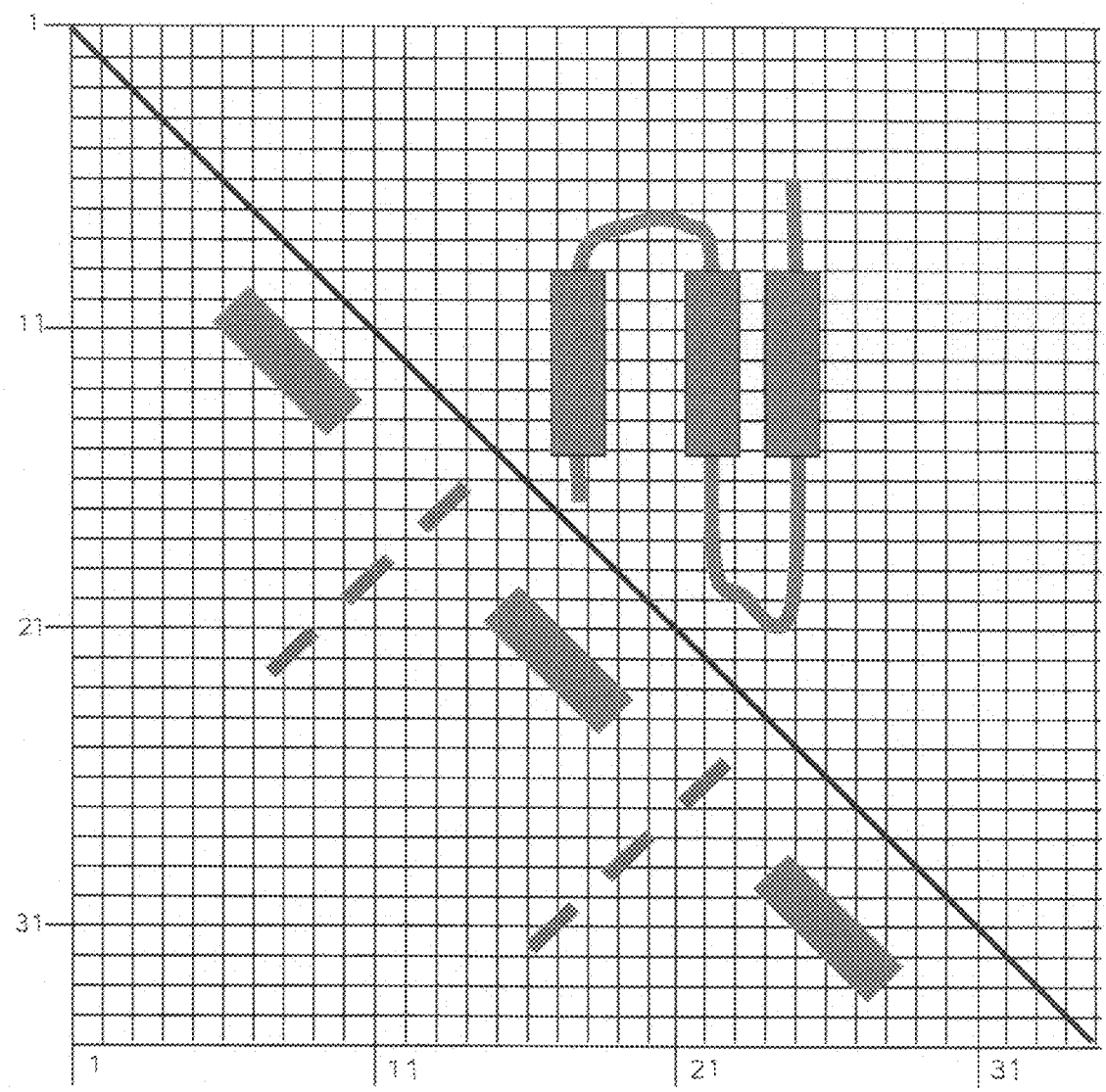
FIG. 7 shows the topology and mapping of a protein that consists of only α-helices. Diagrammatically, the arrangement of the α-helix between local residues appears as the red bars on the map. The topological arrangement of these α-helices with respect to each other is indicated by the brown dotted lines. The dotted line is used because only some of the residues in the adjoining α-helix are actually making contact. In this example, the topological arrangement looks similar to the antiparallel beta sheets shown in FIG. 1.

This can be taken to other structures. In FIG. 6 (parallel β sheets), the structure involves parallel β-strands: $\{1\sim5\}_1$, $\{16\sim20\}_2$ and $\{31\sim35\}_3$. The graph is different because of the way the sequences align. An α-helical structure can also be evaluated in this way (FIG. 7) with the helical segments expressed by the red bars, and their spatial arrangement expressed by the dotted lines running diagonally on the triangle. The topological constraint function ($f_{ij}(\xi)$) plays a primary role with parallel β-sheets because the amino-acid sequence must loop-back-around on itself. If the adjoining sequence lacks a sufficient number of residues, the loop-back-around would tend to bend (stress) the amino acid fragment excessively.

The form of plotting used in this FIG. 5, is used to help understand the output and summarizes the main part of the data storage as vectors. Each structure contains information about the orientation of residues either to the side or above and below. The folder looks for the best assembly of these short fragments using the CLE and the local thermodynamic potentials discussed above.

A Qualitative Description of Protein Folding Based on CLE Model

Here we provide a qualitative description of how the cross-linking entropy affects protein folding according to Eqns (1) through (3). Because proteins tend to fold in a sequential manner (from N to C terminus), one must visualize this process in as dynamic rather than static. Nevertheless, it should be remembered that the folding of a complex structure requires at least as much sequence as the shortest loop of the domain. The entropy loss should be minimized and this usually favors short loops according to Eqn (1). Only a very special type of amino acid sequence can produce a protein where a segment at its N-terminus actually waits while the rest of sequence folds and then hooks on as a β-sheet at the C-terminus.

The hydrophobic effect is a strongly local phenomenon. Secondary structure may form with dominantly extended-like features (70) or even much of the basic secondary structure in tact (5), but the effects of attraction between the two β-strands is only possible when the two strands are in proximity of each other.

Figure 8:
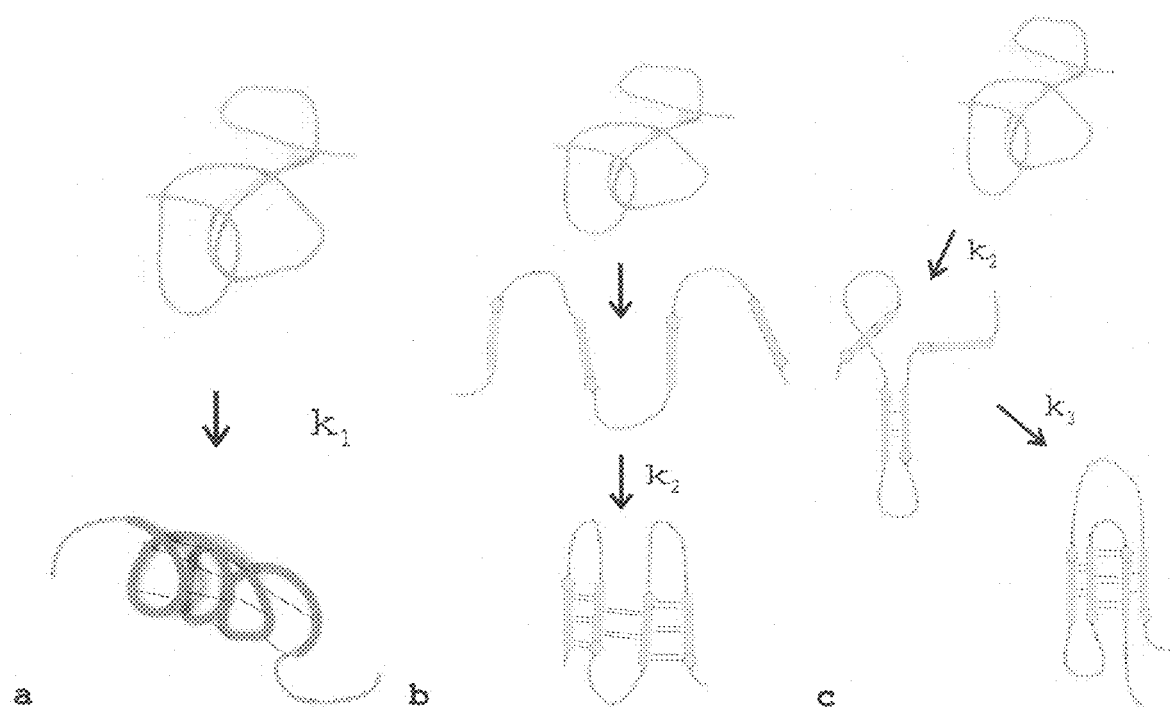
FIG. 8 shows the role of entropy in the formation of different kinds of secondary structure: (a) α-helix, (b) a pleated β-sheet, and (c) a Greek key structure. In these processes, the rate constants are as follows: $k_1 > k_2 > k_3$. For both (a) and (b), the whole structure is formed at roughly the same time and effectively collapses into such a structure. For (c), the folding will first depend on $k_2$, and then on $k_3$ with $k_2 > k_3$.

Qualitatively, the CLE helps discriminate between different folding processes. In FIG. 8, we illustrate this by showing the formation of three different folds: (a) an α-helix, (b) a pleated β-sheet and (c) a Greek key fold.

The cross-links between residues in an α-helix are at every fourth residue so $\Delta G_{ij}$ (Eqn (1)) will be essentially a constant for all α-helix contacts and the formation rate will depend strictly on the local characteristics of the residues. This means the folding rate should be approximately simultaneous over the length of the α-helix in a refolding experiment.

The folding of each loop in the β-sheet of FIG. 8b proceeds independently of the other loops, but $\Delta G_{ij}$ depends on $\Delta N_{ij}$ (Eqn (1)). Proximity is a critical aspect of protein folding rates for β-sheets where the residues i and j that are closest in sequence space ($\Delta N_{ij}$ small implies $\Delta G_{ij}$ small) are also closest in physical space and therefore are more likely to combine sooner. Because the loops are of similar length in FIG. 8b, their approximate rates of formation will be nearly equal in a refolding experiment and for the most part can be considered simultaneous. However, whereas the first fold of FIG. 8c is depicted as the same rate ($k_2$) as FIG. 8b, the second rate ($k_3$) is much slower and will usually occur long after first fold has formed.

It is known that the rate of folding is much different between α-helices and β-sheets (74) where the rate for α-helices is much faster. This is used in the method developed in the CLE model.

Assuming the folding proceeds directly from the denatured state to the native state with no significant kinetic traps along the reaction coordinate, the rate of folding can be expressed as $$k = \left(\frac{k_B T}{h}\right) \exp\left\{-\frac{\Delta G}{RT}\right\} \quad (4)$$

where h is the Planck constant, $k_B T/h$ expresses the vibrational energy of the denatured state (9). We express the cross-link between i and j as (i, j), and we rewrite Eqn (2) in terms of a group of cross-links encompassing a persistence length $\xi$, and the corresponding indices i and j in terms of the effective indices $\tilde{i}$ and $\tilde{j}$ such that $(i, j) \subset (\tilde{i}, \tilde{j})$. Assuming only anti-parallel β-sheets are involved, we can ignore the topological constraint contributions which are mostly necessary in computing parallel β-sheets. Hence, $f_{ij}(\xi)=0$, and the FE becomes $$\Delta G_{cle} = \Delta G_\xi^o + \sum_{all(\tilde{i},\tilde{j})} \langle \Delta G \rangle_{\tilde{i}\tilde{j},\xi} \text{ where} \quad (5)$$

$$\langle \Delta G \rangle_{\tilde{i}\tilde{j},\xi} = \sum_{(i,j)\in(\tilde{i},\tilde{j})} \Delta G_{ij} \quad (6)$$

and $\Delta G_{ij}$ and $\Delta G_\xi^o$ are defined in Eqns (1) through (3).

Qualitatively, the structure in FIG. 8c can be effectively grouped into four independent β-strands forming two β-sheets: $\Delta G_{cle} = \Delta G_\xi^o + \langle \Delta G \rangle_2 + \langle \Delta G \rangle_3$, where $\Delta G_2$ corresponds to the entropy-loss that occurs upon formation of the hairpin β-sheet structure (FIG. 8b, the structure associated with the rate $k_2$), and $\Delta G_3$ correspond to the entropy loss to form the second parallel β-sheet associated with the rate $k_3$ (FIG. 8c). Let the total FE for the protein be defined as $\Delta G_{total} = \Delta G_{local} + \Delta G_{es} + \Delta G_{cle}$, where $\Delta G_{local}$ includes such contributions as the salvation FE, the hydrophobic interactions, and other protein specific local interactions, and $\Delta G_{es}$ contains any long-range electrostatic contributions to the FE. Assuming a reversible reaction, all such thermodynamic potentials only depend on the initial and final states of the system. Moreover, only $\Delta G_{cle}$ is a global quantity, the remaining FE only depends on local short-range interactions (hydrophobicity) or are damped out by the formation of salt bridges (oppositely charged rotors). Hence, for any specified structure the thermodynamic contributions from $\Delta G_{local} + \Delta G_{es}$ can be estimated from the change in the initial and final topology. The long-range contribution of $\Delta G_{es}$ is generally thought to be small due to solvent effects. Hence, the electrostatic contributions also appear to be largely short-range and small. Likewise, $\Delta G_\xi^o$ can be estimated from the flexibility of the structure (30) and, for fixed $\xi$, can be estimated from Eqn (3). The rate determining contributions in this model are therefore $\Delta G_2$ and $\Delta G_3$. If we further assume that these local interactions are the same between the β-strands, the contribution of these interactions will be shared almost equally between the residues and $\Delta G_{total} = 2(\Delta G'_{local} + \Delta G'_{es}) + \Delta G_{cle} = 2\Delta G' + \Delta G_{cle}$, where the prisms indicate the local and electrostatic interactions of the individual cross-links are approximated.

Since, these contributions are separable from the rest of the expression in $\Delta G_{total}$ we can estimate the protein-folding rate to be $$k = \left(\frac{k_B T}{h}\right) \exp\left\{-\frac{\Delta G_{local} + \Delta G_{es} + \Delta G_\xi^o}{RT}\right\} \exp \quad (7)$$

$$\left(-\frac{\langle \Delta G \rangle_2}{RT}\right) \exp\left(-\frac{\langle \Delta G \rangle_3}{RT}\right)$$

$$= (k_B T/h) \exp\{-(A_o + 2A)/RT\} \prod_{all(\tilde{i},\tilde{j})} W_{\tilde{i}\tilde{j},\xi}$$

-continued $$= CB^2 \prod_{all(i,j)} W_{\overline{ij},\xi}$$

where $A=\Delta G'_{local}+\Delta G'_{es}$ is the contribution from the local interaction and is negative quantity for any spontaneous reaction, $A_o=\Delta G_\xi^o$, $C=\exp(-A_o)$, $B=\exp(-A)$, $W_{\overline{ij},\xi}=\exp(-\langle\Delta G\rangle_{\overline{ij},\xi}/RT)$, and $\overline{ij},\xi$ corresponds to the index 2 or 3 in this particular example. From Eqn (7), $k_2=CBW_2$ and $k_3=CBW_3$. Now given that the binding interactions for formation of 2 and 3 are identical, $\langle\Delta G\rangle_{\overline{ij},\xi}$ is a positive-increasing function of $\Delta N_{\overline{ij}}$ and $\Delta G_3 > \Delta G_2 > 0$ in Eqn (7). Therefore, $k_2>k_3$ (FIG. 8c) because $k_3$ corresponds to the longest chain ($\Delta N_2 < \Delta N_3$).

The CLE provides a quantitative physical model with solutions that resemble the contact order model (75), but more than that, the CLE shows why the contact order is a reasonable heuristic in protein and RNA folding. The CLE also predicts that α-helices can fold to any conceivable length (76), and that they fold cooperatively because the contact points and their relative distance along the protein chain are uniform (FIG. 8a) For pleated β-sheets (FIG. 8b), the folding rate of each loop depends on $W_2$ and β-sheet formation shows a distant dependent rate that is usually slower than the α-helix (74): $k_2<k_1$ (FIGS. 8a and b). For the β-meander (FIG. 8b), the folding rate for all the same strand lengths will be of the order of $W_2$ and such identically shaped pleated β-sheet structures will appear to fold cooperatively on the time scale that is proportional to $1/W_2$. In forming structures like a Greek key, the folding rate depends on the product $W_2W_3$. This will be a much longer folding time than the α-helix (FIG. 8a) or the pleated β-sheet (FIG. 8b) structures ($k_3<<k_2$). Further, because this structure has a large entropy loss, few such structures are likely to be found in nature. The Greek key and the jellyroll fold, although existing in nature, are far less common compared to the pleated β-sheet.

EFFECT OF THE INVENTION

Finding the topology of a protein is an essential intermediate step between the simple three-state secondary structure prediction and the final 3D structure of a protein.

Secondary structure in proteins only refers to whether the amino acid sequence has α-helices, β-sheets or coil. Some programs also can indicate whether there is a high probability of a turn. Since there are $2^{n-1}n!/2$ possible ways to arrange this secondary structure (where n is the number of secondary structures), merely assuming all configurations are allowed yields an astronomically large number of structures to test for any real sequence. It costs considerable resource to test them all. Therefore, a powerful approach that can weed out the useless solutions is needed to help drastically reduce unnecessary ways of arranging the secondary structure. The invention has the strong capabilities to assist in research in this direction.

This algorithm is expected to aid the protein structure researcher to find the topology of a protein quickly and effectively. For RNA structure calculations, we have already developed an approach that significantly improves the performance of these calculations over existing standards (30). We have applied it to protein structure calculations here because of the universality of this theory of biopolymer folding. To account for the difference between proteins and RNA, different parameterization and a different folding approach was used.

The invention also helps grant insight into the dominant folding pathway of a protein and can be helpful in understanding the effects of mutations on the topological stability of a protein.

REFERENCES

1. Lesk, A. M. Introduction to protein architecture (book) Oxford university Press, Oxford, 2001, ch 2.
2. Anfinsen, C. B., and Scheraga, H. A. Experimental and theoretical aspects of protein folding (review) *Advances in Protein Chemistry* 29, 205-300, 1975.
3. Richardson, J. S. The Anatomy and taxonomy of protein structure (review) *Advances in Protein Chemistry* 34, 167-339, 1981.
4. Tanford, C. Protein Denaturation (review) *Advances in Protein Chemistry* 23, 121-282, 1968.
5. Laurents, D. V., and Baldwin, R. L. Protein folding: matching theory and experiment (article) *Biophys. J.* 75, 428-34, 1998.
6. Fischer, D., Barret, C., Bryson, K., Elofsson, A., Godzik, A., Jones, D., Karplus, K. J., Kelley, L. A., Maccallum, R. M., Pawowski, K., Rost, B., Rychlewski, L. and Sternberg, M. J. CAFASP-1: Critical assessment of fully automated structure prediction methods (article) *Proteins: Structure, Function and Genetics, Suppl.* 3, 209-217, 1999.
7. Ito, M. *The refolding of the LECT2 cytokine and high dimensional NMR structural analysis.* (Ph.D. thesis), University of Tokyo. Department of Agriculture and Life Science. 2001 (In Japanese).
8. Ito, M., Nagata, K., Kato, Y., Oda, Y., Yamagoe, S., Suzuki, K., and Tanokura, M. Expression, oxidative refolding, and characterization of six-histidine-tagged recombinant human LECT2, a 16-kDa cheotactic protein with three disulfide bonds (article) *Protein Expression and Purification* 27, 272-8, 2003.
9. Fersht, A. *Structure and mechanism in protein science: a guide to enzyme catalysis and protein folding* (book) Freeman, New York, 1998.
10. Wüthrich, K. *NMR of proteins and nucleic acids* (book) Wiley-Interscience, New York, 1986.
11. Cavanagh, J., Fairbrother, W. J., Palmer, A. G., and Skelton, N. J. *Protein NMR Spectroscopy: principles and practice* (book) Academic Press, Tokyo, 1996.
12. Delaglio, F., private communication.
13. Sippl, M. J., Weitckus, S., Floeckner, H. In search of protein folds (article) *The Protein Folding Problem and Tertiary Structure Prediction* (Merz, K., Le Grand, S. eds) Birkhauser, Boston, 1994, pp. 353-407.
14. Smith, T. F., Lo Conte, L., Bienkowska, J., Gaitatzes, Ch., Rogers, R. G., and Lathrop, R. Current limitations to protein threading approaches (article) J. Comp. Biol. 4, 217-225, 1997.
15. Levitt, M., Gerstein, M., Huang, E., Subbiah, S., and Tsai, J. Protein folding: the end game (article) *Annu. Rev. Biochem.* 66, 549-79, 1997.
16. Chung, S. Y., and Subbiah, S., The use of side-chain packing methods in modeling bacteriophage repressor and cro proteins (article) Protein Science 4:2300-9, 1995.
17. Lemer C. M., Rooman M. J., Wodak S. J., Protein structure prediction by threading methods: evaluation of current techniques, Proteins: Struct. Funct. Genet., 23:337-55, 1995.
18. McGuffin L J, Jones D T. Improvement of the GenTHREADER method for genomic fold recognition (article) Bioinformatics 19, 874-81, 2003.

19. McGuffin L J, Bryson K, Jones D T. The PSIPRED protein structure prediction server (article) *Bioinformatics* 16, 404-405, 2000.
20. Jones D T. Protein secondary structure prediction based on position-specific scoring matrices (article) *J. Mol. Biol.* 292, 195-202, 1999.
21. Leach, A. R. *Molecularmodeling: principles and applications* (book) Longman, Essex, 1996.
22. Kal, L., Skeel, R., Bhandarkar, M., Brunner, R., Gursoy, A., Krawetz, N., Phillips, J., Shinozaki, A., Varadarajan, K., and Schulten, K. NAMD2: Greater scalability for parallel molecular dynamics (article) *J. Computational Phys.* 151, 283-312, 1999.
23. Kollman, P., Dixon, R., Cornell, W., Fox, T., Chipot C., and Pohorille, A. The development/application of a 'minimalist' organic/biochemical molecular mechanic force field using a combination of ab initio calculations and experimental data (contributed article) *Computer Simulation of Biomolecular Systems*, Vol. 3 A. Wilkinson, P. Weiner, W. Van Gunsteren, eds. Elsevier, Amsterdam, 1997, pp. 83-96.
24. Weiner, S. J., Kollman, P. A., Case, D. A., Singh, U. C., Ghio, C., Alagona, G., Profeta, S., and Weiner, P. A new force field for molecular mechanical simulation of nucleic acids and proteins (article) *J. Am. Chem. Soc.* 106, 765-784, 1984.
25. Brooks, B. R., Bruccoleri, R. E., Olafson, B. D., States, D. J., Swaminathan, S., and Karplus, M. A Program for Macromolecular Energy, Minimization, and Dynamics Calculations (article) *J. Comp. Chem.* 4, 187-217, 1983.
26. MacKerell Jr., A. D., Brooks, B., Brooks III, C. L., Nilsson, L., Roux, B., Won, Y., and Karplus. M. The Energy Function and Its Parameterization with an Overview of the Program (article) In The Encyclopedia of Computational Chemistry. 1:271-277, P. v. R. Schleyer et al., editors. John Wiley & Sons: Chichester, 1998.
27. Cohen, F. E., Sternberg, M. J. E., and Taylor, W. R. Analysis and prediction of the packing of α-helices against a β-sheet in the tertiary structure of globular proteins (article) *J. Mol. Biol.* 156, 821-862, 1982.
28. Cohen, F. E., Sternberg, M. J. E., and Tayler, W. R. Analysis and prediction of protein β-sheet structures by a combinatorial approach (article) *Nature* 285, 378-82, 1980.
29. Levitt M. Protein folding by restrained energy minimization and molecular dynamics (article) *J Mol Biol.* 170, 723-64, 1983.
30. Dawson, W K., Suzuki, K., and Yamamoto, K. A physical origin for functional domain structure in nucleic acids as evidenced by cross linking entropy. Parts I and II. (articles) *J. Theor. Biol.* 213:359-386 and 387-412, 2001.
31 Rose, G. D. Getting to know U (editorial) *Advances in Protein Chemistry*, Eisenberg, D. S., Kuriyan, J., and Richards, F. M. eds. 62, xv-xxi, 2002.
32. Rose, G. D. Turns in peptides and proteins (review) *Advances in Protein Chemistry* 37, 1-109, 1985.
33. Rost, B. Predicting one-dimensional protein structure by profile based neural networks (article) *Meth. in Enzym.* 266, 525-39, 1996.
34. Rost, B., and Sander, C. Prediction of protein secondary structure at better than 70% accuracy (article) *J. Mol. Biol.* 232, 584-599, 1993.
35. Rost, B., and Sander, C. Combining evolutionary information and neural networks to predict protein secondary structure (article) *Proteins* 19, 55-77, 1994.
36. Rost, B. TOPITS: Threading One-dimensional Predictions Into Three-dimensional Structures (article) *The third international conference on Intelligent Systems for Molecular Biology (ISMB)*, (C Rawlings, D Clark, R Altman, L Hunter, T Lengauer, and S Wodak, eds.). Cambridge, England, Menlo Park, Calif.: AAAI Press, 1995, pp. 314-321.
37. Rost, B, Schneider, R, and Sander, C. Protein fold recognition by prediction-based threading (article) *J. Mol. Biol.* 270, 471-80, 1997.
38. Cuff, J. A. and Barton, G. J. Evaluation and Improvement of Multiple Sequence Methods for Protein Secondary Structure Prediction (article) *Proteins: Structure, Function and Genetics* 34, 508-519, 1999.
39. Cuff, J. A. and Barton, G. J. Application of Enhanced Multiple Sequence Alignment Profiles to Improve Protein Secondary Structure Prediction (article) *Proteins: Structure, Function and Genetics* 40, 502-511, 2000.
40. Kelley, L A., MacCallum, R M. and Sternberg, M J E. Enhanced genome annotation using structural profiles in the program 3Dpssm (article) *J. Mol. Biol.* 299, 499-520, 2000.
41. Kelley, L. A., Maccallum, R., and Sternberg, M. J. E. Recognition of remote protein homologies using three-dimensional information to generate a position specific scoring matrix in the program 3DPSSM. (article) *RECOMB* 99, Proceedings of the Third Annual Conference on Computational Molecular Biology. Editors: Sorin Istrail, Pavel Pevzner, and Michael Waterman. The Association for Computing Machinery: New York, 1999, pp. 218-225.
42. McClelland, J. L., and Rumelhart, D. E. (article) Explorations in Parallel Distributed Processing. vol 3. MIT Press, Cambridge, 1988, pp 318-362.
43. Kneller, D. G., Cohen, F. E., and Langridge, R. Improvements in Protein Secondary Structure Prediction by an Enhanced Neural Network (article) *J. Mol. Biol.* 214, 171-182, 1990.
44. Ngo, J. T., Marks, J., and Karplus, M. Computational Complexity, Protein Structure Prediction, and the Levinthal Paradox (contributed article) *The Protein Folding Problem and Tertiary Structure Prediction* (Merz, K, and LeGrand, S. eds.) Birkhauser, Boston, 1994, pp. 433-506.
45. Levitt, M. A simplified representation of protein conformations for rapid simulation of protein (article) *J Mol Biol.* 104, 59-107, 1976.
46. Frauenfelder, H., and Leeson, D. T. The energy landscape in non-biological and biological molecules (article) *Nature Structural Biology* 5, 757-9, 1998.
47. Pappu, R. V., Srinivasan, R., and Rose, G. D. The Flory isolated-pair hypothesis is not valid for polypeptide chains: implications for protein folding (article) *Proc. Natl. Acad. Sci. USA.* 97, 12565-70, 2000.
48. Flory, P. J. *Statistical Mechanics of Chain Molecules* (book) New York, Wiley Interscience, 1969.
49. Shortle, D. E. Staphylococcal nuclease: a showcase of m-value effects (review) *Advances in Protein Chemistry* 46, 217-47, 1995.
50. Lim, W. A., and Sauer, R. T. The role of internal packing interactions in determining the structure and stability of a protein (article) *J. Mol. Biol.* 219, 359-76, 1991.
51. Fisher, M. E. Effect of excluded volume on phase transitions in biopolymers (article) *J. Chem. Phys.* 45, 1469-73, 1966.
52. Dill, K. A., and Stigter, D. Modeling protein stability as heteropolymer collapse (review) *Advances in Protein Chemistry* 46, 59-104, 1995.

53. Honig, B. and Yang, A.-S. Free energy balance in protein folding (review) *Advances in Protein Chemistry* 46, 27-58, 1995.
54. Bilsel, O., and Matthews, R. C. Barriers in protein folding reactions (article) *Advances in Protein Chemistry* 53, 153-207, 2000.
55. Lazaridis, T., and Karplus, M. Effective energy function for protein is solution (article) *Proteins: structure, function, and genetics* 35, 133-52, 1999.
56. Huang, E. S., Subbiah, S., Tsai, J. and Levitt, M. Using a hydrophobic contact potential to evaluated native and near-native folds generated by molecular dynamics simulations (article) *J. Mol. Biol.* 257, 716-25, 1996.
57. Leszczynski, J. F. and Rose, G. D. Loops in globular proteins: a novel category of secondary structure (article) *Science* 234, 849-855, 1986.
58. Wilson, I. A., and Stanfield, R. L. Antibody-antigen interactions: new structures and new conformational changes (article) *Current Opinion in Structural Biology* 4, 857-67, 1994.
59. Braden, B. C., Goldbaum, F. A., Chen, B.-X., Kirschner, A. N., Wilson, S. R., and Erlanger, B. F. X-ray crystal structure of an anti-Buckminsterfullerene antibody Fab fragment: Biomolecular recognition of $C_{60}$ (article) *Proc. Natl. Acad. Sci.* (*USA*) 97, 12193-97, 1996.
60. Chou, P. Y., and Fasman, G. D. Prediction of protein conformation (article) *Biochemistry* 13, 222-45, 1974.
61. Chan, A. W. E., Hutchinson, E. G., Harris, D. and Thornton, J. M. Identification, classification, and analysis of beta-bulges in proteins (article) *Protein Science* 2, 1574-90, 1993.
62. Richardson, J. S., Getzoff, E. D., and Richardson, D. C. The β-bulge: a common small unit of non-repetitive protein structure (article) *Proc. Natl. Acad. Sci.* (*USA*) 75, 2574-8, 1978.
63. Chou, K.-C. Prediction of tight turns and their types in proteins (article) *Analytical Biochemistry* 286, 1-16, 2000.
64. Chothia, C. Conformation of twisted β-pleated sheets in proteins (article) *J. Mol. Biol.* 75, 295-302, 1973.
65. Garnier, J., Osguthrope, and Robson, B. Analysis of the accuracy and implications of simple methods for predicting the secondary structure of globular proteins (article) *J. Mol. Biol.* 120, 97-120, 1978.
66. Robson, B. and Osguthorpe, D. J. Refined models for computer simulation of protein folding (article) *J. Mol. Biol.* 132, 19-51, 1979.
67. Lindley, I. J. D. Interleukin-8 (contributed chapter) *Cytokines* Mire-Sluis, A., and Thorppe, R. Eds. Academic Press, New York, 1998, ch 8.
68. Yamagoe, S., Mizuno, S., and Suzuki, K. Molecular cloning of human and bovine LECT2 having a neutrophil chemotactic activity and its specific expression in the liver. (article) *Biochim Biophys. Acta* 1396, 105-113, 1998.
69. Yamagoe, S., Kameoka, Y., Hashimoto, K., Mizuno, S., and Suzuki, K. Molecular cloning, structural characterization, and chromosomal mapping of the human LECT2 gene (article) *Genomics* (article) 48, 324-329, 1998.
70. Pappu, R. V., and Rose, G. D. A simple model for polyproline II structure in unfolded states of alanine-based peptides (article) *Protein Science* 11, 2437-55, 2002.
71. Baldwin, R. L., and Rose, G. D. Is protein folding hierarchic? parts I. & II. (article) *Trends in Biological Science* 24, 26-33, 1999.
72. Delaglio, F., Grzesiek, S., Vuister, G. W., Zhu, G., Pfeifer, J. and Bax, A. NMRPipe: a multidimensional spectral processing system based on UNIX pipes (article) *J. Biomol. NMR.* 6, 277-293, 1995.
73. Cornilescu, G., Delaglio, F., and Bax, A. Protein backbone angle restraints from searching a database for chemical shift and sequence homology (article) *J. Biomol. NMR* 13, 289-302, 1999.
74. Hofrichter, J., Thompson, P. A., Munoz, V., Jas, G. S., Henry, E., Hagen, S. J., Lapius, L., and Eaton, W. A. Dynamics of α-helices, β-hairpins and loops (contributed article) *Old and New Views of Protein Folding* (Kuwajima, K., and Arai, M. eds.) Elsevier, Amsterdam, 1999, pp. 53-65.
75. Debe, D. A., and Goddard, W. A. First principles prediction of protein folding rates (article) *J. Mol. Biol.* 294, 619-625, 1999.
76. Baldwin, R. L., and Zimm, B. H. Are denatured proteins ever random coils? (article) *Proc. Natl. Acad. Sci.* (*USA*). 97, 12391-2, 2000.

What is claimed is:

1. A method to predict the topology of the spatial arrangement of an amino acid sequence comprising:
  using an entropy evaluation model that takes into account the global contributions of entropy to the folding of a protein (herein referred to by the name cross linking entropy (CLE) model) combined with other thermodynamic potentials as a protein-folding model to predict said topology, wherein using said entropy evaluation model to predict said topology comprises the following steps:
  A. inputting an amino acid sequence of said protein,
  B. preparing information on secondary structure of said amino acid sequence by way of at least one theoretical or experimental estimate,
  C. applying the CLE model to said amino acid sequence and secondary structure information to evaluate the free energy of a combinatorial number of β-strand and α-helix arrangements performed in polynomial time defined by $c(n-1)(n+1)$ wherein c is a constant and n is the number of secondary structure elements found in said amino acid in step A and prepared in step B,
  D. applying the CLE model in conjunction with other thermodynamic potentials that approximate hydrophobic, electrostatic and polar interactions in a thermodynamic calculation to account for both short and long range folding interactions and predict a minimum free energy and corresponding topology of the said amino acid sequence,
  E. applying the CLE model to predict the global folding kinetics information of said amino acid sequence, and
  F. storing the global folding kinetics information in a data file or in other form of digital memory, wherein steps A. through F. are performed with a computer.

2. A method according to claim 1, in which the cross linking entropy (CLE) model is used to evaluate the entropy loss of said protein due to folding into a particular topology given a known secondary or estimated secondary structure.

3. A method according to claim 2, in which an initial theoretical estimate of the secondary structure is obtained from either a theoretical source, or an experimental source.

4. A method according to claim 3, in which said initial theoretical estimate is from an experimental source that is an NMR experiment, an x-ray crystallography experiment, or both.

5. A method according to claim 4, in which the theoretical estimate is further supplemented with sequence alignment to find regions in which conserved segments remain essentially unchanged by differences in the aligned sequences.

6. A method to predict the topology of the spatial arrangement of an amino acid sequence, comprising:

using an entropy evaluation model that takes into account the global contributions of entropy to the folding of a protein (herein referred to by the name cross linking entropy (CLE) model) combined with other thermodynamic potentials as a protein-folding model to predict said topology, wherein the cross linking entropy (CLE) model is used to evaluate the entropy loss of said protein due to folding into a particular topology given a known secondary or estimated secondary structure, an initial theoretical estimate of the secondary structure is obtained from either a theoretical source, or an experimental source, said experimental source is an NMR experiment or x-ray crystallography, or both, and said amino acid sequence and secondary structure information is used to calculate the free energy of a combinatorial number of β-strand and α-helix arrangements performed in polynomial time defined by c(n−1)(n+1), wherein c is a constant and n is the number of secondary structure elements found in said amino acid; and further comprising storing the results of the free energy calculation in a data file or in other form of digital memory, wherein steps of the method are performed with a computer.

7. A method to predict the topology of the spatial arrangement of an amino acid sequence comprising the following steps:

A. inputting an amino acid sequence of a protein,

B. preparing information on secondary structure of said amino acid sequence by way of at least one theoretical or experimental estimate, C. applying a CLE model to approximate the global folding kinetics of the said amino acid sequence, D. applying the CLE model to said amino acid sequence and secondary structure information to reduce the combinatorial number of β-strand and α-helix arrangements, E. applying the CLE model in conjunction with other thermodynamic potentials that approximate hydrophobic, electrostatic and polar interactions in a thermodynamic calculation to optimize the free energy to find the most thermodynamically favorable topology for said amino acid sequence, wherein the global free energy (FE) contribution from the CLE between two distinct amino acid residues, herein labeled i and j, is calculated by equation (1):

$$\Delta G_{ij}^{gcle} = -T\Delta S_{ij}^{gcle} = \frac{\gamma k_B T}{\xi}\left\{\ln\left(\frac{2\gamma\xi\Delta N_{ij}}{3\lambda_{ij}^2}\right) - 1 + \frac{3\lambda_{ij}^2}{2\gamma\xi\Delta N_{ij}}\right\} \quad (1)$$

wherein, i and j represent the indices of two distinct residues in said amino acid sequence, and j>i, $\Delta N_{ij}=j-i+1$ expresses the number of residues separating i and j, $\Delta G_{ij}^{gcle}$ is the difference in the free energy contribution to the global CLE from residues i and j transitioning from the denatured (random flight) state to the native state, $\Delta S_{ij}^{gcle}$ is the corresponding global entropy loss, $\xi$ is the persistence length, $\gamma$ is a dimensionless weight parameter describing the self-avoiding properties of a polymer chain, $k_B$ is the Boltzmann constant, T is the temperature, and $\lambda_{ij}$ (the bond gap) expresses the amino acid separation distance between the center of mass of residue i and the center of mass of residue j when both are treated as isolated molecules, and wherein the total CLE contribution to the free energy ($\Delta G_{cle}$) is calculated by equation (2):

$$\Delta G_{cle} = \Delta G_\xi^o + \sum_{all\_bonds(i,j)} \Delta G_{ij} + \sum_{i',j'} f_{i'j'}(\xi) \quad (2)$$

wherein, $\Delta_{ij}^{gcle}$ is defined in equation (1), i' and j' are indices specifying two secondary structure elements (α-helices or β-strands) that are joined together by the corresponding set of bonds i and j, $f_{i'j'}(\xi)$ is a positive definite penalty function used to enforce topology constraints on the minimum allowed sequence length of a loop connecting two elements of secondary structure i'j' and is a function of the persistence length $\xi$, and $\Delta G_\xi^o$ is a renormalization correction and is an integral function of $\xi$ as shown by equation (3):

$$\Delta G_\xi^o = \frac{(\gamma+1/2)Nk_BT}{D\xi}\int_{+1}^{\xi}\left(\frac{\ln(x)}{(1-x)}+1\right)dx \quad (3)$$

wherein, N indicates the number of amino acids in the said sequence, D is the dimensionality of the system, the limits in the integral (1→ξ) indicate the change in the number of degrees of freedom from an individual amino acid residue to a cluster of $\xi$ amino acids treated as a group (where $\xi$>1 amino acid and $\xi$ need not be an integer) and x is a variable in the integral for values in the range of 1 to $\xi$, and F. storing the most thermodynamically favorable topology information in a data file or in other form of digital memory, wherein steps A through F are performed with a computer.

8. A method according to claim 6, in which the CLE model is applied in conjunction with other derived or constructed thermodynamic potentials that approximate hydrophobic, electrostatic and polar interactions, in a thermodynamic calculation to account for both short and long range folding interactions and predict a minimum free energy and corresponding topology of said amino acid sequence.

9. A method for building a 3D structure of a protein for molecular dynamics simulation comprising: generating, using a computer, a topology for said protein by the method according to claim 1 or 7; and constructing, using a computer, a 3D structure from the topology.

* * * * *